United States Patent
Kirsch et al.

(10) Patent No.: US 7,105,708 B2
(45) Date of Patent: *Sep. 12, 2006

(54) METHOD FOR PRODUCING COMPOUNDS HAVING A CF$_2$O BRIDGE

(75) Inventors: Peer Kirsch, Darmstadt (DE); Andreas Taugerbeck, Darmstadt (DE); Alexander Hahn, Ruesselsheim (DE)

(73) Assignee: Merck Patentgesellschaft, Darmstadt (DE)

( * ) Notice: Subject to any disclaimer, the term of this patent is extended or adjusted under 35 U.S.C. 154(b) by 64 days.

This patent is subject to a terminal disclaimer.

(21) Appl. No.: 10/450,266

(22) PCT Filed: Nov. 26, 2001

(86) PCT No.: PCT/EP01/13721

§ 371 (c)(1),
(2), (4) Date: Jun. 12, 2003

(87) PCT Pub. No.: WO02/48073

PCT Pub. Date: Jun. 20, 2002

(65) Prior Publication Data

US 2004/0059137 A1    Mar. 25, 2004

(30) Foreign Application Priority Data

Dec. 12, 2000  (DE) ................ 100 61 790
Dec. 23, 2000  (DE) ................ 100 64 996
Feb. 2, 2001   (DE) ................ 101 05 313

(51) Int. Cl.
*C07C 41/01*    (2006.01)
*C07C 43/18*    (2006.01)
*C07C 43/20*    (2006.01)

(52) U.S. Cl. .................. 568/655; 656/663; 656/669

(58) Field of Classification Search ................ 428/1.1; 252/299.63; 549/20, 21, 22, 35, 36, 39; 570/127; 568/655, 656, 663, 669
See application file for complete search history.

(56) References Cited

U.S. PATENT DOCUMENTS 5,792,386 A    8/1998  Matsui et al.

6,187,223 B1    2/2001  Andou et al.
6,787,062 B1 *  9/2004  Kirsch et al. .......... 252/299.63
6,875,894 B1 *  4/2005  Kirsch et al. ............. 568/38
6,916,940 B1 *  7/2005  Kirsch et al. ............ 549/348

FOREIGN PATENT DOCUMENTS

| EP | 0786445 | 7/1997 |
| EP | 08442229 | 5/1998 |
| WO | WO 0164667 | 9/2001 |

OTHER PUBLICATIONS

CA 89:75224, 1978.*
CA 101: 54289, 1984.*
Haas A. et al.: "Synthese seitenkettenfluorierter aromatischer Verbindungen und deren chemische Reaktivität ," Chemische Berichte., Bd. 121, Nr. 7, 1988, Seiten 1329-1240, XP002189374.
Sondej SC et al.: "Gem-Difluoro compounds: a convenient preparation from ketones and aldehydes by halogen fluoride treatment of 1,3-dithiolanes," Journal of Organic Chemistry, American Chemical Society. Easton, US Bd. 51, 1986, Seiten 3508-3513, XP002085716.
Seebach D. et al.: "Zur Umpolung der Carbonylreaktivität; Deprotonierung von Ketenthioacetalen zu 1,1-dithiosubstituierten Allyl-und Pentadienyllithium-verbindungen sowie deren Reaktionen mit Elektrophilen," Liebigs Annalender Chemie., Bd.5, 1977, Seiten 811-829, XP002189375.
Kirsch P. et al.: "Difluorooxymethylene-bridged liquid crystals: a novel synthesis based on the oxidative alkoxydifluorode sulfuration of dithianylium salts," Angewandte Chemie. International Edition., Bd. 4, Nr. 8, Apr. 2001 Seiten 1480-1484, XP002189376.

* cited by examiner

*Primary Examiner*—Shean C. Wu
(74) *Attorney, Agent, or Firm*—Millen, White, Zelano & Branigan, P.C.

(57) ABSTRACT

The invention relates to a process for the preparation of compounds containing at least one —CF$_2$—O— bridge in the molecule, in which a) an acid is added onto at least one ketene dithioketal, b) the resultant bis(alkylthio)carbenium salt is reacted with at least one compound having at least one hydroxyl group in the presence of a base, c) and subsequently, preferably in situ, the resultant dithioorthoester is subjected to oxidative fluorodesulfurisation using a fluorinating agent and an oxidant to give the compound containing at least one —CF$_2$—O— bridge in the molecule.

23 Claims, No Drawings

METHOD FOR PRODUCING COMPOUNDS HAVING A CF₂O BRIDGE

The invention relates to a process for the preparation of compounds containing at least one —CF₂—O— bridge in the molecule. The invention furthermore relates to ketene dithioketals and bis(alkylthio)carbenium salts as starting compounds in the process according to the invention. The invention furthermore relates to novel compounds containing at least one —CF₂—O— bridge in the molecule which are obtainable by the process according to the invention.

Compounds containing one, two or more —CF₂—O— bridges can be used, in particular, as liquid crystals, but also as pharmaceuticals, crop-protection agents or as precursors for products of this type or for the preparation of polymers.

Liquid-crystalline compounds containing one or more —CF₂—O— bridges are advantageously suitable as components of liquid-crystalline media, as used in optical and electro-optical display elements, such as TN-, STN and TFT-LCDs. Thus, for example, EP 0 844 229 A1 describe liquid-crystalline compounds which contain an —O—CF₂— bridge. Various processes are proposed for the preparation of this —O—CF₂— bridge. According to one of the processes described, firstly an aromatic halide is converted into a Grignard compound or into a lithiated compound and then converted into the dithiocarboxylic acid using carbon disulfide. The dithiocarboxylic acid is converted into a thioester using a phenol in the presence of an alkali metal hydride and iodine. The desired —O—CF₂— bridge is then formed from the thioester using a fluorinating agent.

According to another process, it is proposed firstly to react a cyclohexanone with hexamethylphosphoric triamide and dibromodifluoromethane in order to obtain a difluorohexylidene derivative. Bromine is firstly added onto the latter, which is then etherified by reaction with a phenoxide with simultaneous elimination of hydrogen bromide with formation of a —CF₂—O— bridge.

The disadvantage of this process is that the reaction rates are low, the yields are unsatisfactory, and the work-up and purification of the product are complex.

It is therefore an object of the invention to provide a process for the preparation of compounds having at least one —CF₂—O— bridge in the molecule which starts from readily accessible starting materials, does not require isolation of intermediates, and gives the products in good yields.

It is a further object of the invention to indicate starting compounds and intermediates for the process according to the invention and to provide advantageous processes for the preparation of the starting compounds.

It is a further object of the invention to describe novel products obtainable by the process according to the invention.

The object is achieved by a process according to Claim 1. The sub-claims relate to advantageous variants of this process.

The invention thus relates to a process of the type mentioned at the outset, in which
  a) an acid is added onto at least one ketene dithioketal,
  b) the resultant bis(alkylthio)carbenium salt is reacted with at least one compound having at least one hydroxyl group in the presence of a base,
  c) and subsequently, preferably in situ, the resultant dithioorthoester is subjected to oxidative fluorodesulfurisation using a fluorinating agent and an oxidant to give the compound containing at least one —CF₂—O— bridge in the molecule.

An advantage of the process according to the invention is the ready accessibility of the ketene dithioketals as starting compounds. Furthermore, the ketene dithioketals can readily be obtained in high purity due to their generally good crystallisation properties, which is particularly important for the synthesis of high-purity liquid crystals.

A further advantage of this process is the acid addition onto the ketene dithioketals, which can be carried out even under very mild conditions. This enables access to alkylbis (alkylthio)carbenium salts which contain sensitive functional groups, such as esters, nitrites or ketals. In addition, it is also possible to convert compounds containing two or more ketene dithioketal functions per molecule into compounds correspondingly containing two or more —CF₂O— bridges.

Furthermore, the oxidative fluorination to give the compound containing a —CF₂—O— group is carried out under very mild, slightly basic conditions and is therefore, in contrast to the conventional methods, compatible with a multiplicity of unprotected functional groups, for example a nitrile group.

In addition, it is a particular advantage of the process according to the invention that the reaction starting from the ketene dithioketal via the carbenium salt and the dithioorthoester to give the product containing at least one —CF₂O— bridge can be carried out in a reaction mixture, i.e. without isolation and purification of the intermediates. The yields that can be achieved here are high to very high.

The invention furthermore relates to ketene dithioketals and to the corresponding bis(alkylthio)carbenium salts, in particular those according to Claims 20, 21, 23, 24 and 26. These substances are particularly advantageously suitable as starting compounds for use in the process according to the invention for the preparation of liquid-crystalline compounds themselves or of compounds which can be used in the synthesis of liquid-crystalline compounds.

The invention furthermore relates to novel compounds containing at least one —CF₂—O— bridge in the molecule, in particular those according to Claims 22 and 25, which are obtainable by the process according to the invention. These compounds are themselves novel liquid-crystalline compounds or can advantageously be used as synthetic building blocks for the preparation of liquid-crystalline compounds.

A novel diketone and the ketals accessible therefrom, in particular those according to Claim 27, are likewise a subject-matter of the invention. The diketone and the corresponding ketals are starting compounds in the synthesis of the said ketene dithioketals according to preferred process variants.

Preferred variants of the process according to the invention are described below.

The process according to the invention is preferably carried out employing ketene dithioketals of the formula II

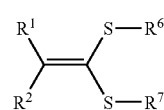

II

In this formula:
R¹ and
R², independently of one another, are straight-chain, branched or cyclic alkyl having from 1 to 25 carbon atoms, where $R^1$ and $R^2$ may be bridged to one another in such a way that the

group is a cyclic alkyl having from 4 to 8 carbon atoms in the ring, preferably a cyclohexane, and/or in which one or more H atoms may be replaced by halogen, —CN or further substituted or unsubstituted alkyl and/or aryl radicals, and/or in which one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and/or aryl, which may be monosubstituted or polysubstituted by halogen, straight-chain, branched and/or cyclic alkyl and/or aryl, which may likewise be substituted, and in which one or more CH groups may be replaced by N, where one of the radicals $R^1$ and $R^2$ may alternatively be H, $R^6$ and $R^7$, independently of one another, are straight-chain, branched or cyclic alkyl having from 1 to 12 carbon atoms, where $R^6$ and $R^7$ may be bridged to one another in such a way that the

group is a 4- to 8-membered ring, and/or in which one or more H atoms may be replaced by halogen or further substituted or unsubstituted alkyl and/or aryl radicals, and/or in which one or more non-adjacent —CH$_2$— groups may be replaced, independently of one another, by —CO—, —O—, —S—, —CH=CH—, —C≡C—, —NH— or —N(CH$_3$)—, and/or aryl, which may be monosubstituted or polysubstituted by halogen or straight-chain, branched and/or cyclic alkyl and/or aryl.

$R^6$ and $R^7$ are preferably bridged to one another in such a way that the

group is in the form of a 5- to 7-membered ring

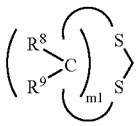

in which $R^8$ and $R^9$ are H or a substituted or unsubstituted alkyl or alkenyl group having from 1 to 6 carbon atoms, where the

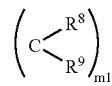

group may form a cycloalkyl or aryl group, and m1 is 2, 3 or 4.

Above and below, the

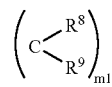

and/or

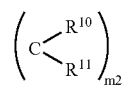

groups, in which $R^{10}$, $R^{11}$ and m2 are as defined for $R^8$, $R^9$ and m1 respectively, are preferably ethylene, propylene or 2,2-dimethylpropylene.

The acid to be added onto the ketene dithioketal is preferably an acid HY in which $Y^-$ is a non-coordinating or weakly coordinating anion. $Y^-$ here is preferably a halide, tetrafluoroborate, hexafluorophosphate, perchlorate or alkyl- or arylcarboxylate or alkyl- or arylsulfonate anion, where one, a number or all of the H atoms in the alkyl or aryl groups may be substituted by fluorine or chlorine. Particularly preferred acids are trifluoromethanesulfonic acid and a tetrafluoroboric acid/diethyl ether complex.

The acid is employed in an approximately equimolar amount based on the ketene dithioketal units to be reacted. The reaction with the acid HY is advantageously carried out at a temperature in the range from −80 to +30° C. in an inert polar solvent or solvent mixture. Suitable solvents are, for example, ethers or haloalkanes, such as diethyl ether, tetrahydrofuran, dichloromethane or trichloromethane.

Addition of an acid HY onto the ketene dithioketal of the formula II gives a bis(alkylthio)carbenium salt of the formula III

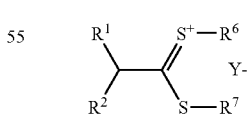

III in which $R^1$, $R^2$, $R^6$, $R^7$ and $Y^-$ are as defined above.

It is particularly advantageous that the formation of the bis(alkylthio)carbenium salt by addition of the acid onto the ketene dithioketal is reversible. On use of 4-substituted cyclohexylideneketene dithioketals, the trans-substituted cyclohexane derivatives of the bis(alkylthio)carbenium salt, which are thermodynamically favoured over the cis-configuration, and thus trans-substituted cyclohexane compounds containing a —CF$_2$O— bridge, can thus be obtained with very high selectivity.

For equilibration to give the thermodynamically more favourable isomer, it is therefore advantageous to stir the reaction mixture comprising ketene dithioketal, acid and corresponding carbenium salt for an extended time, in particular from 15 minutes to 6 hours or even longer, at a temperature of from −80 to +50° C., in particular from −30 to +50° C.

The two synthetic steps following the first reaction are preferably carried out in situ, i.e. using the reaction mixture from the first reaction and thus without isolation of the intermediates.

The compound containing at least one hydroxyl group with which the bis(alkylthio)carbenium salt is reacted is not subject to any particular restrictions per se regarding its structure. However, since the process according to the invention is particularly suitable for the preparation of liquid crystals themselves or of synthetic building blocks for liquid crystals, the radical proposed in the compound containing at least one hydroxyl group is preferably designed in such a way that it contains structural units which find use in liquid crystals.

The compound containing at least one hydroxyl group is preferably an alkyl or aryl alcohol of the formula IV R$^3$—OH (IV), in which the alkyl or aryl radical R$^3$ may be substituted as desired.

The hydroxyl compound is preferably used in a molar excess of up to 2-fold, in particular up to 1.5-fold, based on the theoretical amount to be employed. The reaction with the hydroxyl compound is carried out in the presence of at least one base, preferably at a temperature in the range from −100 to +50° C. Bases which are advantageously suitable for this purpose are organic nitrogen bases, in particular tertiary amines, such as, for example, triethylamine, pyridine or pyridine derivatives. The base is advantageously employed in a molar ratio of from 1:1 to 2:1, based on the hydroxyl compound. Suitable solvents are, in particular, polar solvents or solvent mixtures, as already indicated above.

Reaction of the bis(alkylthio)carbenium salt of the formula III with the hydroxyl compound of the formula IV gives a dithioorthoester of the formula VI

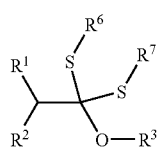
VI in which R$^1$, R$^2$, R$^6$, R$^7$ and R$^3$ are as defined above.

Starting from the ketene dithioketal of the formula II via the bis(alkylthio)carbenium salt of the formula III obtainable by addition of the acid HY and via the dithioorthoester of the formula VI which is accessible by reaction with the hydroxyl compound of the formula IV, the compound of the formula V containing at least one —CF$_2$—O— bridge can be prepared in accordance with the invention as indicated in reaction scheme 1.

Reaction scheme 1:

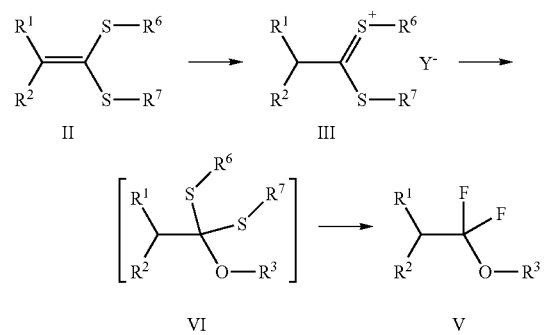

The orthoester VI is generally not isolated, but instead converted directly into the compound V by oxidation.

Oxidants which can be used are conventional oxidants. The oxidant employed is preferably a compound which liberates halonium equivalents. Examples of oxidants are N-chlorosuccinimide, N-bromosuccinimide, N-iodosuccinimide, 1,3-dibromo-5,5-dimethylhydantoin, dibromoisocyanuric acid, bromine and chlorine. Particular preference is given to bromine since the bromides which form can easily be separated off. Likewise suitable are, for example, SO$_2$Cl$_2$, SO$_2$ClF, nitrosonium and nitronium salts and chloramine-T. The nitrosonium and nitronium salts may also, if desired, be prepared in situ from suitable precursors, for example from inorganic or organic nitrites and/or nitrates.

Fluorinating agents which can be employed are conventional fluorinating agents. The fluorinating agent is particularly preferably selected from the group formed by hydrogen fluoride, aliphatic and aromatic amine/hydrogen fluoride complexes, such as, for example, pyridine/hydrogen fluoride complexes, in particular HF in pyridine having an HF content of from 50 to 70%, and triethylamine/, melamine/ and polyvinylpyridine/hydrogen fluoride complexes.

The reaction with the oxidant and fluorinating agent is advantageously carried out at a temperature of from −100 to +50° C. Suitable solvents are likewise the solvents and solvent mixtures indicated above.

The entire conversion of the ketene dithioketal into the product containing at least one —CF$_2$O— bridge is particularly preferably carried out as a so-called one-pot process, i.e. without isolation and purification of the carbenium salt and/or the dithioorthoester as intermediates.

The compound containing at least one hydroxyl group preferably has the formula IVa

IVa in which

R$^c$ is H, halogen, —CN, —NCS, —SF$_5$ or alkyl having from 1 to 18 carbon atoms, in which, in addition, one or two non-adjacent —CH$_2$— groups may be replaced by —O—, —S—, —CO—, —O—CO—, —CO—O—, -E- and/or —C≡C—, and/or in which, in addition, one or more H atoms may be replaced by halogen and/or —CN, E is CR$^4$=CR$^5$ or CHR$^4$—CHR$^5$, R$^4$ and R$^5$ are each, independently of one another, H, alkyl having 1–6 carbon atoms, F, Cl, Br, CF$_3$ or CN, and Z$^3$ is —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, and A$^3$ is 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where one or more H atoms in these groups may be substituted by halogen, —CN and/or alkyl having from 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and r is 0, 1 or 2, with the proviso that, in the case where r=0, R$^c$ has the indicated meaning of alkyl, but in which the carbon atom in the 1-position is not replaced by a heteroatom.

A$^3$ is preferably 1,4-phenylene, which may be substituted in the 2-, 3-, 4- and/or 5-position as indicated, preferably by fluorine.

In the case where r=0, the hydroxyl compound is preferably an alkanol, which may be substituted. Particular preference is given to halogenated alkanols, for example trifluoromethanol, trifluoroethanol and trichloroethanol.

According to a further preferred variant of the process according to the invention, the compound containing at least one hydroxyl group has two hydroxyl groups.

The reaction according to the invention with two identical or two different bis(alkylthio)carbenium salts can, with dihydroxyl compounds of this type, give compounds which have two —CF$_2$—O— bridges.

According to this variant, the dihydroxyl compound preferably has the formula IVd

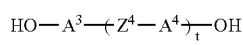

IVd in which A$^3$ is as defined above, and A$^4$ and Z$^4$ have one of the meanings indicated for A$^3$ and Z$^3$ respectively, and t is 0, 1 or 2.

The ketene dithioketal is very particularly preferably obtained from a carbonyl compound. The carbonyl compound may be described by the formula I

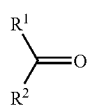

I in which R$^1$ and R$^2$ are as defined above.

The ketene dithioketals are accessible from the carbonyl compounds in a simple manner and in high yields by processes known per se. Reference may be made here by way of example to D. J. Ager, Org. React. 1990, 38, 1–223, in particular pages 63, 95 and 96. It is advantageous that the carbonyl compounds may additionally contain acid-labile substituents. As already mentioned at the outset, it is a further advantage that the ketene thioketals obtainable therefrom can generally be purified easily due to their good crystallisation properties, but nevertheless have good solubility in conventional organic solvents.

A preferred process here is the reaction of a carbonyl compound with a 2-silyl-1,3-dithiane, which may be substituted. Particular preference is given here to the use of 2-trimethylsilyl-1,3-dithiane. The reaction is preferably carried out in the presence of a deprotonating compound, such as alkyl-lithium, for example n-butyllithium. An advantageous range for the reaction temperature is from −130 to 0° C. Suitable solvents are the solvents and mixtures indicated above.

Preferred carbonyl compounds here are those of the formula Ia, which, owing to the structural units present, are advantageously suitable for the preparation of liquid-crystalline compounds or building blocks for liquid-crystal synthesis,

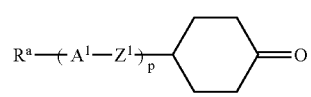

Ia

In this formula,

R$^a$ is H, halogen, —CN or alkyl having from 1 to 18 carbon atoms, in which, in addition, one or two non-adjacent —CH$_2$— groups may be replaced by —O—, —S—, —CO—, —O—CO—, —CO—O—, -E- and/or —C≡C—, and/or in which, in addition, one or more H atoms may be replaced by halogen and/or CN, E is CR$^4$=CR$^5$ or CHR$^4$—CHR$^5$, R$^4$ and R$^5$ are each, independently of one another, H, alkyl having 1–6 carbon atoms, F, Cl, Br, CF$_3$ or CN, and Z$^1$ is —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, and A$^1$ is 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where one or more H atoms in these groups may be substituted by halogen, —CN and/or alkyl having from 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and p has the value 0, 1 or 2.

In the case of the meaning of alkyl in the groups or substituents indicated above or below, in particular in $R^a$, $R^b$, $R^c$ and/or $R^d$, the alkyl radical may be linear or branched. It preferably has 1, 2, 3, 4, 5, 6, 7 or 8 carbon atoms. It is preferably linear and therefore is in particular methyl, ethyl, propyl, butyl, pentyl, hexyl, heptyl or octyl. A branched alkyl radical may be chiral or achiral. Preferred chiral alkyl radicals are 2-butyl (=1-methylpropyl), 2-methylbutyl, 2-methylpentyl, 3-methylpentyl, 2-ethylhexyl, 2-propylpentyl and 2-octyl. Preferred achiral alkyl radicals are isopropyl, isobutyl (=methylpropyl) and isopentyl (=3-methylbutyl). The alkyl radicals may be substituted in the manner indicated.

On use of carbonyl compounds of the formula Ia and hydroxyl compounds of the formula IVa, the —$CF_2$—O-bridged compounds of the formula Va are readily accessible by the process according to the invention. This synthetic route is described with reference to reaction scheme 2, in which the formula IIa denotes the ketene dithioketals and the formula IIIa denotes the corresponding carbenium salts.

In reaction scheme 2 and the following reaction schemes, the dithioorthoester intermediate is in each case not shown explicitly for reasons of clarity.

Reaction scheme 2

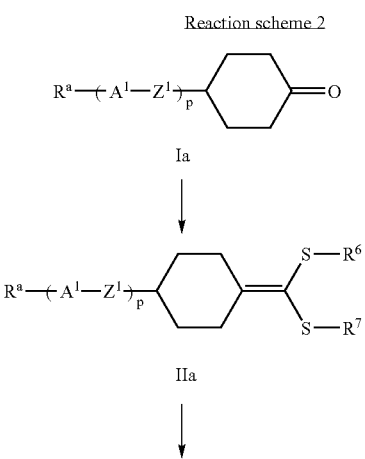

-continued

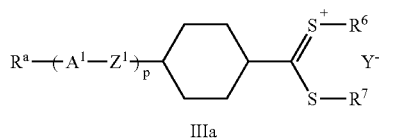

IIIa

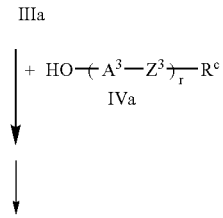

IVa

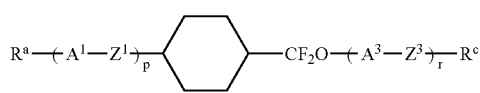

Va

If, instead of the hydroxyl compound of the formula IVa, the dihydroxyl compound of the formula IVd described above is employed, two identical or different bis(alkylthio) carbenium salts of the formulae IIIa and IIId can be added on, giving, after the oxidative fluorodesulfurisation as shown in reaction scheme 3, compounds of the formula Vd containing two $CF_2$—O bridges. These carbenium salts are accessible from the carbonyl compounds Ia and Id via the corresponding ketene dithioketals of the formulae IIa and IId.

$R^{10}$, $R^{11}$, m2, $Z^2$, $A^2$, q, $R^b$ and $Y'^-$ below each have one of the meanings indicated for $R^8$, $R^9$, m1, $Z^1$, $A^1$, p, $R^a$ and $Y^-$ respectively.

Reaction scheme 3

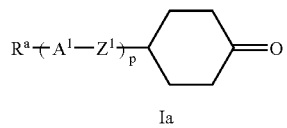

Ia

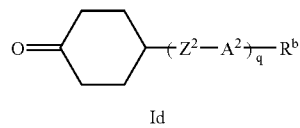

Id

-continued
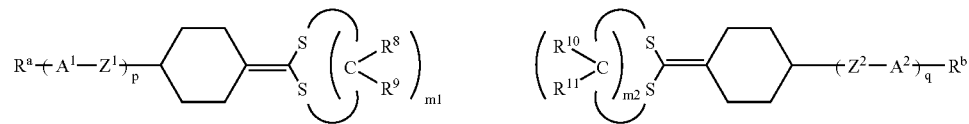
IIa    IId
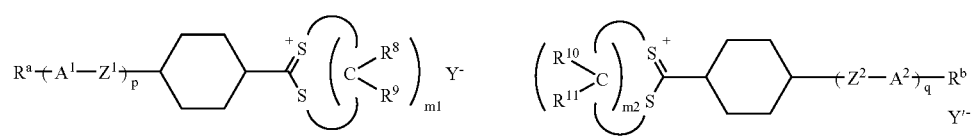
IIIa    IIId
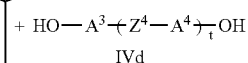
IVd
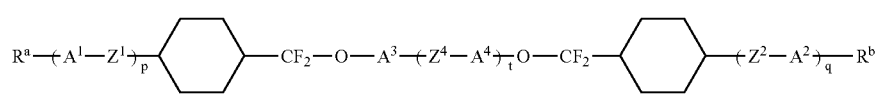
Vd Further preferred carbonyl compounds are those having two or more carbonyl groups.

Two particularly preferred dicarbonyl compounds here are cyclohexanedione of the formula Ib

Ib and the biscyclohexanone compound of the formula Ic

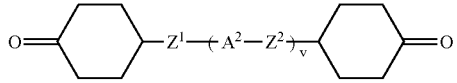

Ic in which $Z^1$ and $Z^2$ each, independently of one another, have one of the meanings indicated for $Z^1$, and $A^2$ has one of the meanings indicated for $A^1$, and v has the value 0, 1 or 2.

Using compounds of this type containing two or more carbonyl functions, compounds containing two or more —$CF_2$—O— bridges in the molecule can be obtained in accordance with a first variant of the process according to the invention. The corresponding intermediates have two or more ketene dithioketal functions and two or more carbenium functions per molecule.

According to a second variant of the process according to the invention, one or more carbonyl groups of a carbonyl compound of this type are protected as a ketal before the conversion into the corresponding ketene dithioketal, with at least one carbonyl group remaining unprotected for conversion into the ketene dithioketal. The compounds accessible therefrom have, besides one or more —$CF_2$—O— bridges, additionally one or more carbonyl functions, if desired protected as the ketal. In particular in the liquid-crystal synthesis, the free carbonyl function can advantageously be used to build up a substituted or unsubstituted alkyl, alkenyl or alkoxy group.

The ketal here is preferably the

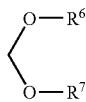

group, with the indicated meanings for $R^6$ and $R^7$.

$R^6$ and $R^7$ are preferably bridged to one another in such a way that the

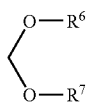

group is in the form of a 5- to 7-membered ring

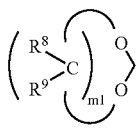

in which $R^8$, $R^9$ and m1 are as defined above.

Reaction scheme 4 illustrates, starting from the cyclohexanedione of the formula Ib, the first variant of the process, according to which compounds of the formula Vb2 containing two —$CF_2$—O— bridges are obtained via the intermediate IIb2 containing two ketene dithioketal functions and IIIb2 containing two carbenium functions by the addition reaction of two identical or different hydroxyl compounds of the formulae IVa and IVb followed by oxidative fluorodesulfurisation.

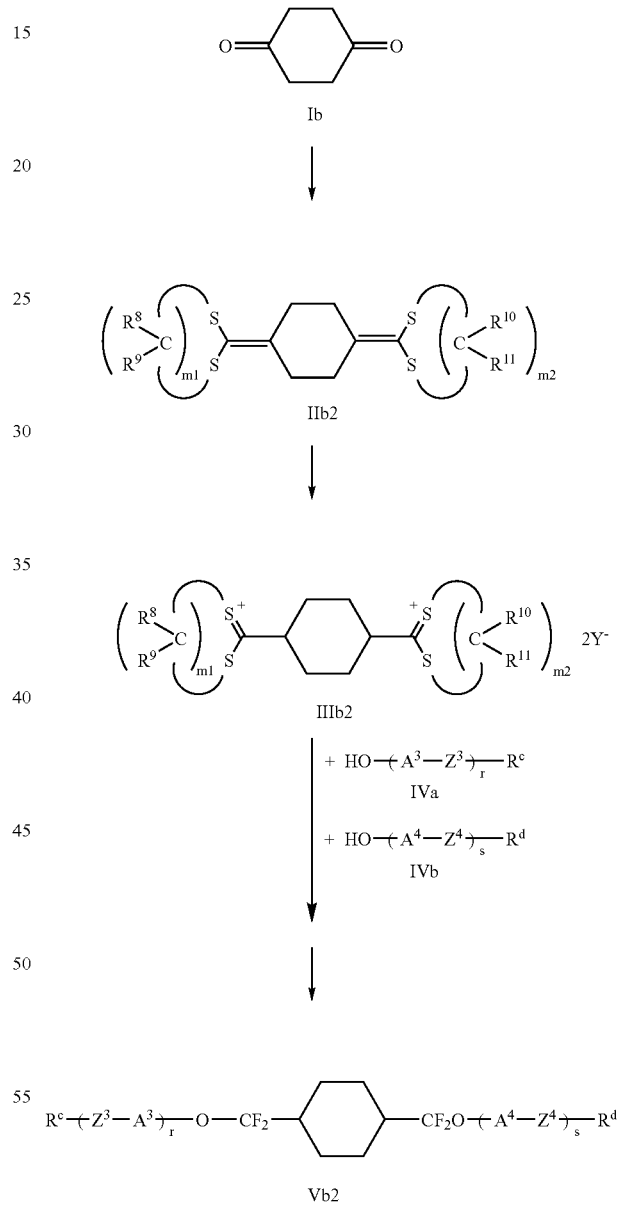

Reaction scheme 4

In an analogous manner starting from biscyclohexanediones of the formula Ic via the bisketene dithioketals IIc2 and the biscarbenium salts IIIc2 by the addition reaction of the two identical or different hydroxyl compounds IVa and IVb, compounds of the formula Vc2 containing two —$CF_2$—O— bridges are obtained (reaction scheme 5).

Reaction scheme 5
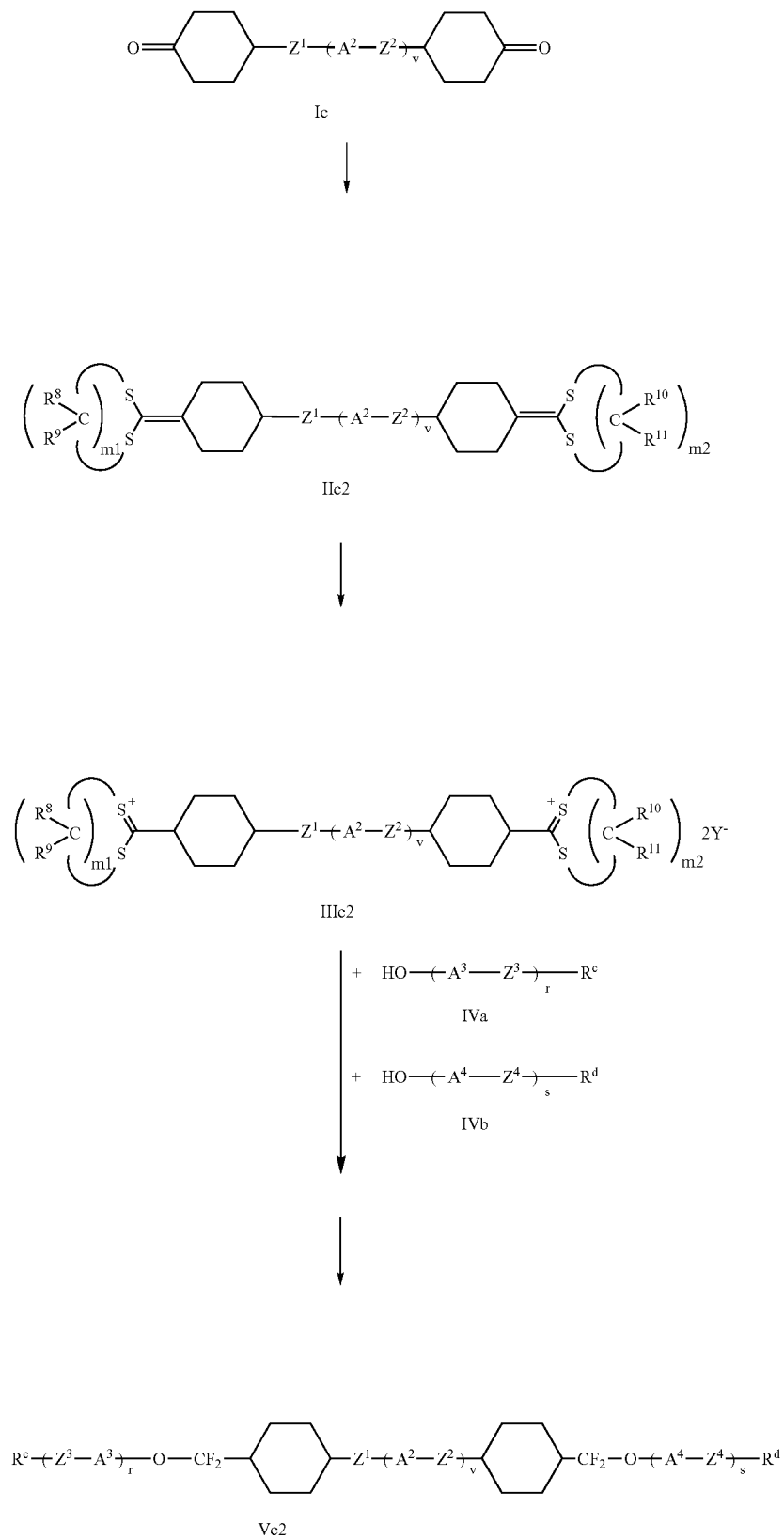

The second variant of the process using cyclohexanedione is illustrated with reference to reaction scheme 6. In the first step, a carbonyl function of the cyclohexanedione of the formula Ib is protected as the ketal by processes known to the person skilled in the art. The resultant compound of the formula Ib1 containing a free carbonyl group is converted in accordance with the invention into the ketene dithioketal IIb1 and further into the bis(alkylthio)carbenium salt IIIb1, onto which a hydroxyl compound of the formula IVa is added. The compound of the formula Vb1 obtained after oxidative fluorodesulfurisation contains a —CF$_2$—O— bridge and a carbonyl group protected as the ketal. The compound Vb1 can serve directly further as synthetic building block, for example in liquid-crystal synthesis, or, as shown here, the ketal is cleaved by processes known to the person skilled in the art to give the free carbonyl function in the compound of the formula Vb.

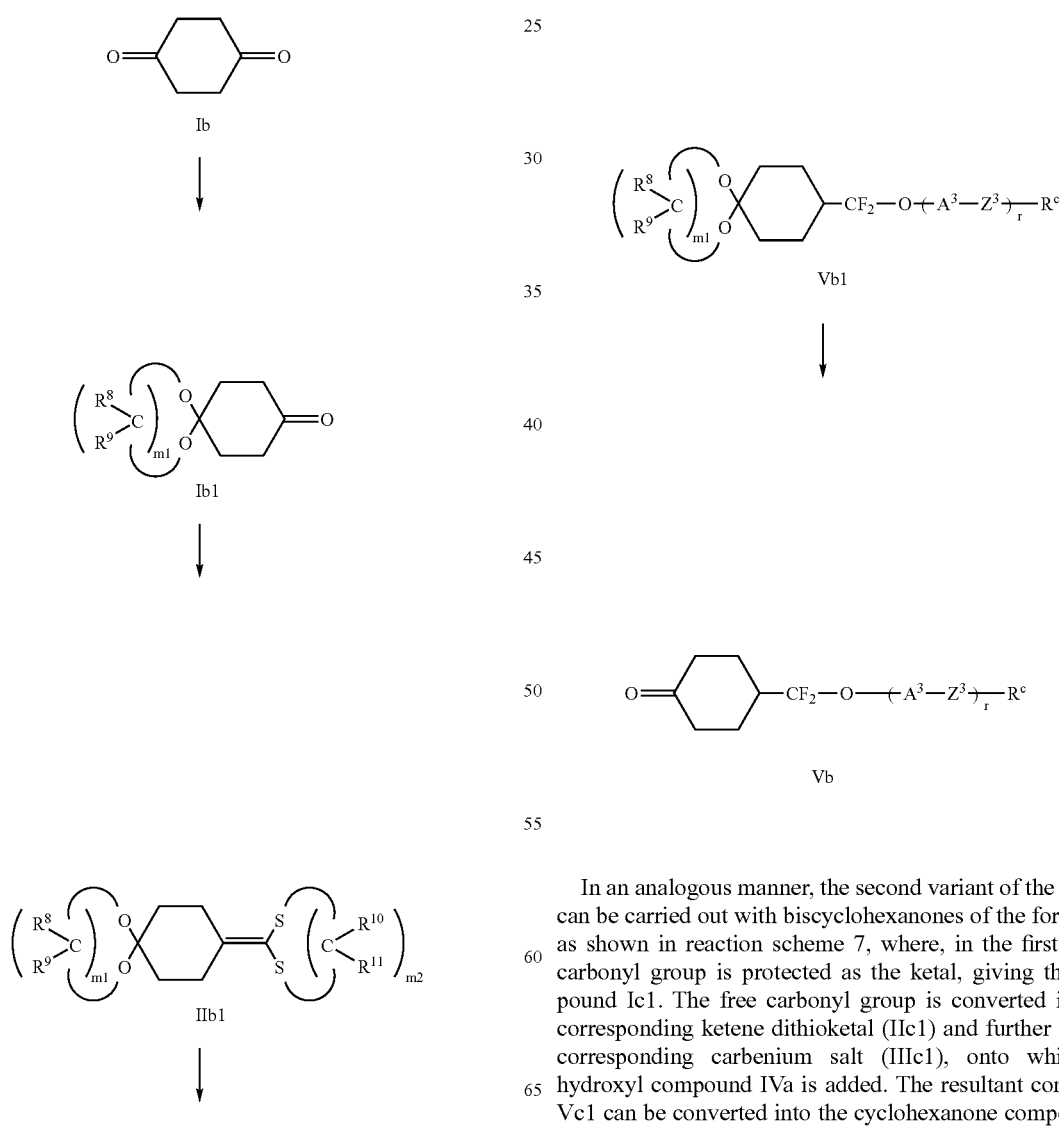

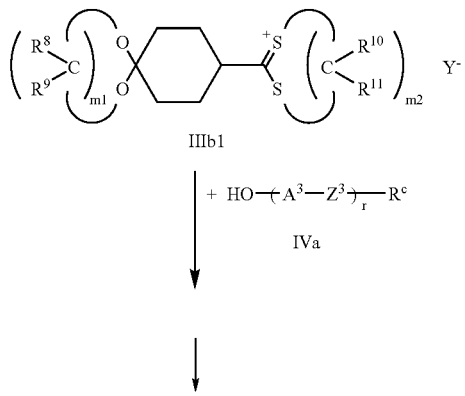

In an analogous manner, the second variant of the process can be carried out with biscyclohexanones of the formula Ic as shown in reaction scheme 7, where, in the first step, a carbonyl group is protected as the ketal, giving the compound Ic1. The free carbonyl group is converted into the corresponding ketene dithioketal (IIc1) and further into the corresponding carbenium salt (IIIc1), onto which the hydroxyl compound IVa is added. The resultant compound Vc1 can be converted into the cyclohexanone compound of the formula Vc by cleavage of the ketal.

Reaction scheme 7
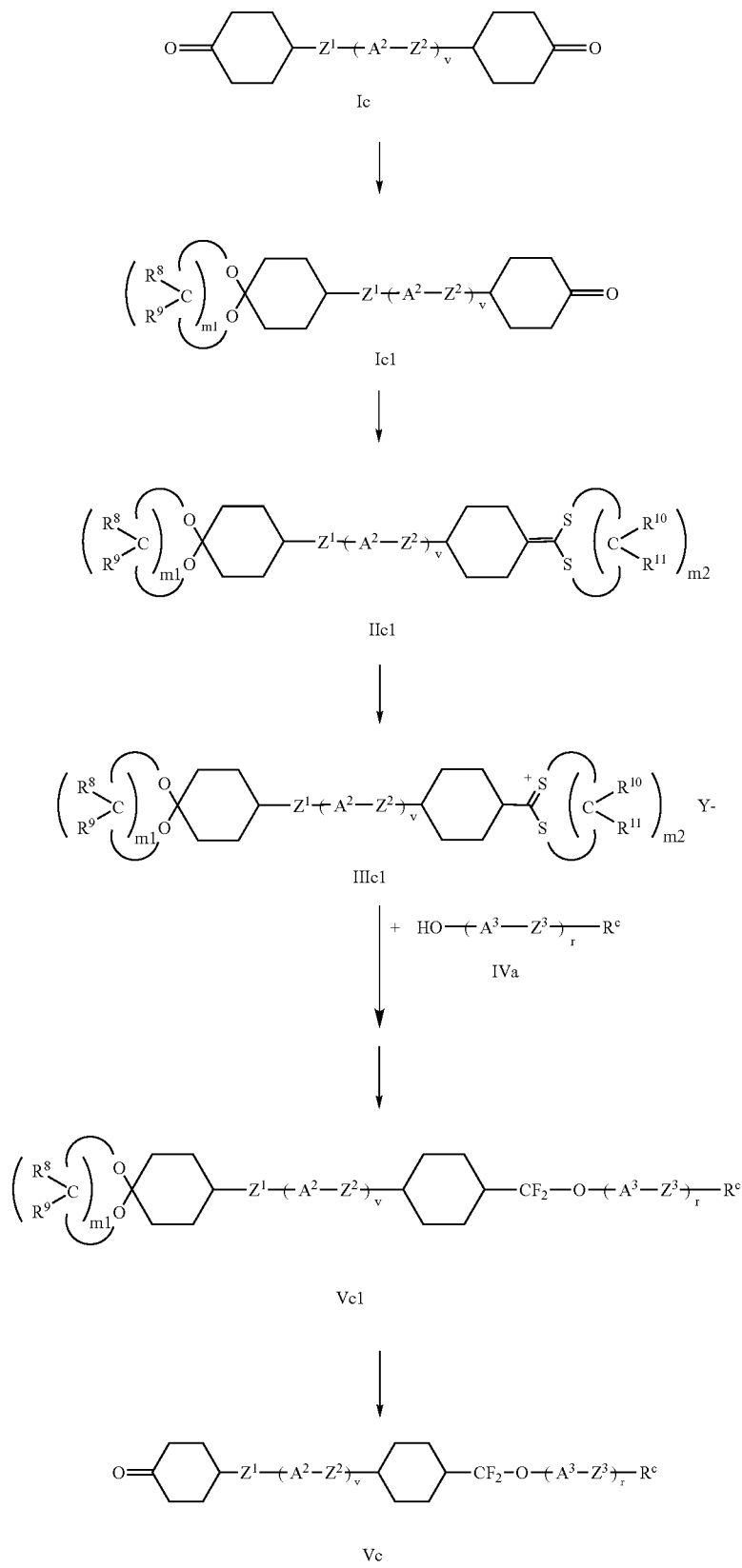

The process according to the invention is generally suitable for the preparation of compounds containing one, two or more —CF$_2$—O— bridges, such as, for example, liquid crystals, precursors for polymers, pharmaceuticals and crop-protection agents. However, it is particularly suitable for the preparation of liquid-crystalline compounds.

Preferred liquid-crystalline compounds which are advantageously accessible by the process according to the invention are shown below, where R$^a$, R$^b$, R$^c$, Z$^1$, Z$^2$ and p are as defined above.

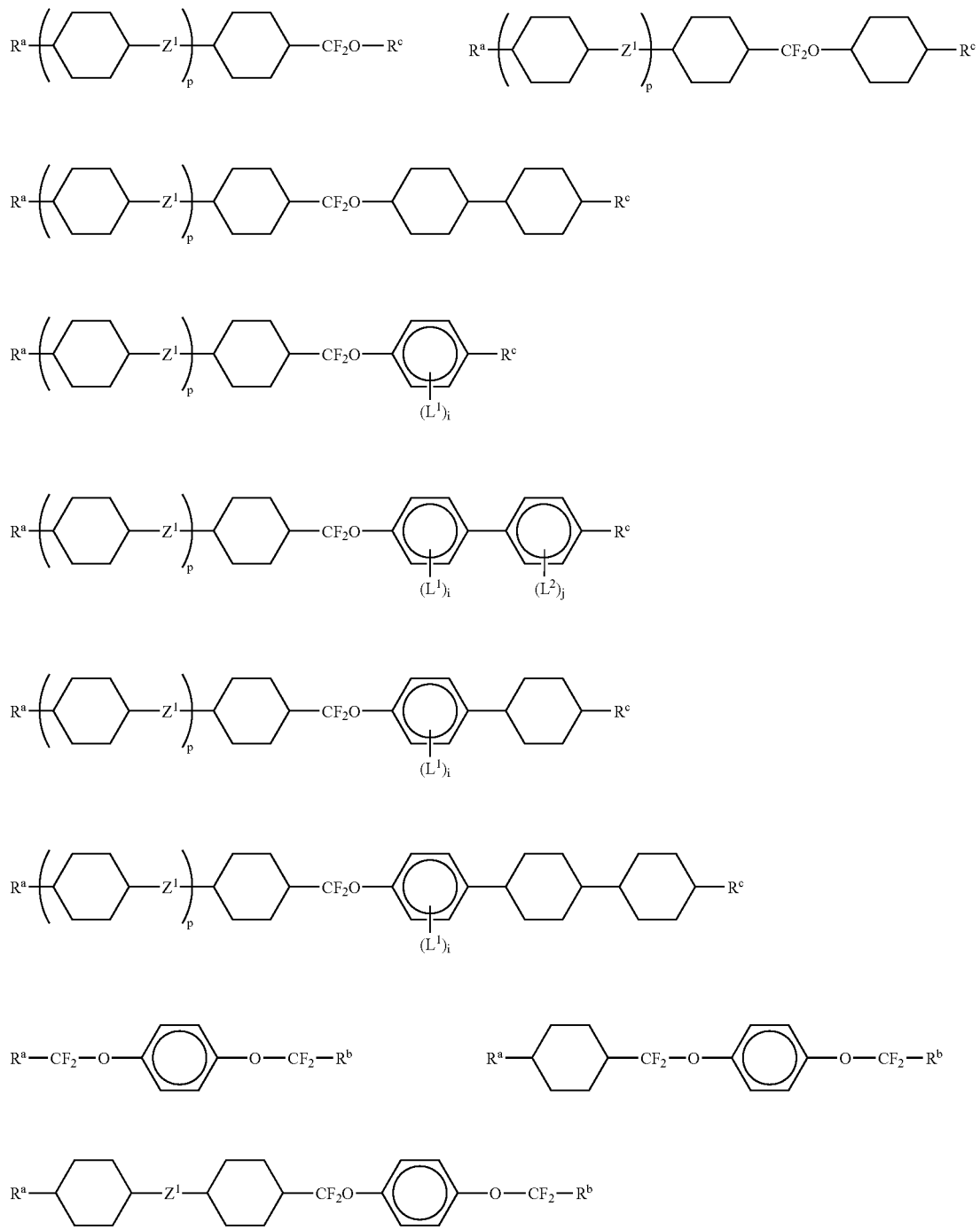

-continued

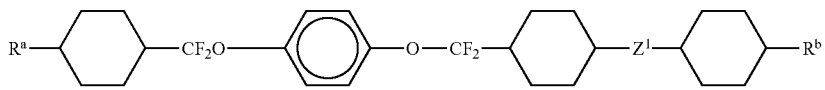

Above and below, $L^1$ and $L^2$, independently of one another, are F, Cl, or an alkyl, alkenyl, alkoxy and/or alkenyloxy group having from 1 to 6 carbon atoms, in which one or more H atoms may be substituted by fluorine, and i and j, independently of one another, are 0, 1, 2, 3 or 4, preferably 0, 1 or 2.

The groups

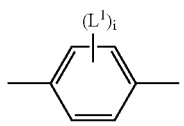

and/or

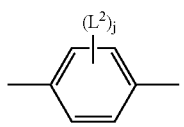

are preferably

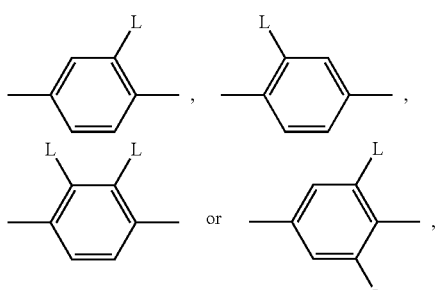

where L has one of the meanings indicated for $L^1$ and $L^2$, in particular F.

The preferred novel starting materials and intermediates in the process according to the invention and the preferred novel products obtainable by the process according to the invention, which together represent a subject-matter of the invention, are explained in greater detail below.

Besides the novel ketene dithioketals, bis(alkylthio)carbenium salts and compounds containing at least one —$CF_2O$— bridge shown above and below, the corresponding dithioorthoesters which can be derived thereof are also covered by the invention.

Above and below, preferred compounds containing at least one 1,4-substituted cyclohexylene group are those in which this group is trans-substituted.

Preferred ketene dithioketals and the corresponding carbenium salts derived therefrom, which are advantageously suitable as starting materials for liquid-crystal synthesis are shown below:

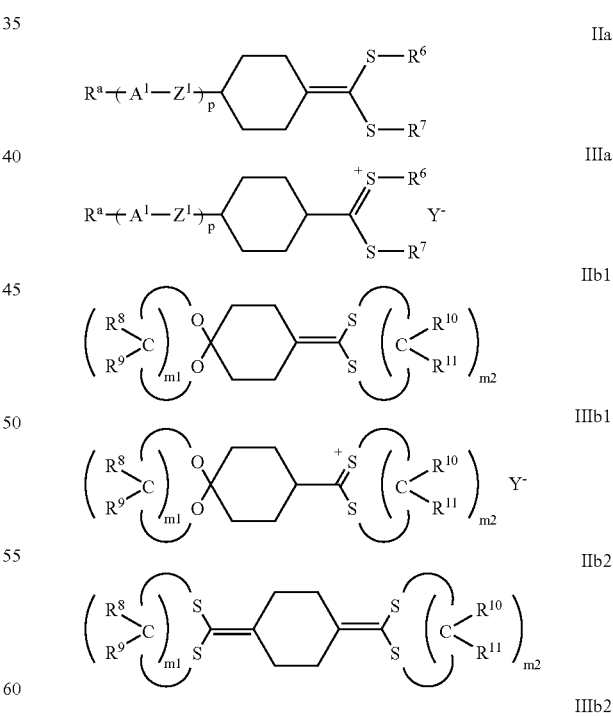

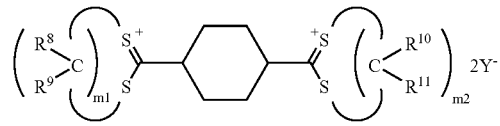

IIc1

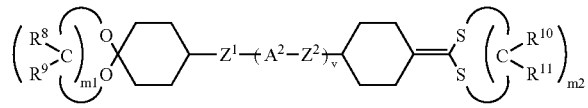

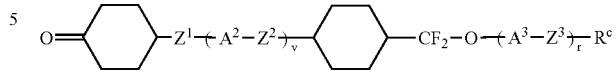
Vc

IIIc1

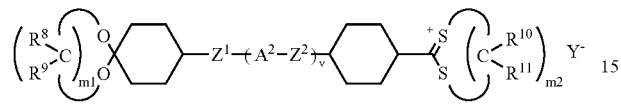

Of the compounds of the formulae Vb1 and Vb, the following carbonyl compounds are preferred:

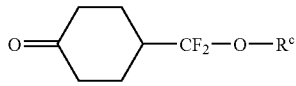

IIc2

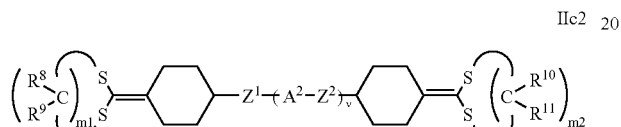

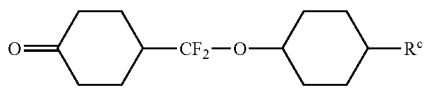

IIIc2

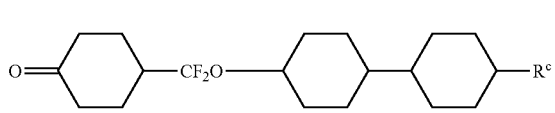

Above and below, the substituents, groups and indices used in the formulae for the compounds according to the invention are each as already defined above for the process according to the invention.

Novel products are, in particular, those obtainable by the process according to the invention which contain both at least one —CF$_2$O— bridge and at least one carbonyl group, which may be protected as the ketal. Of these, preference is given to those compounds which contain a cyclohexanone group. The particularly preferred compounds thereof are indicated below:

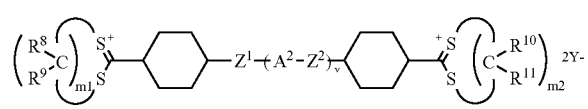

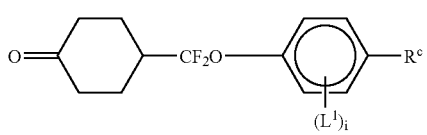

Vb1

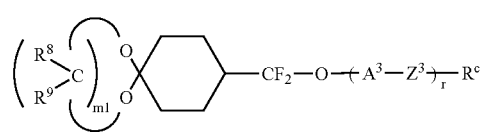

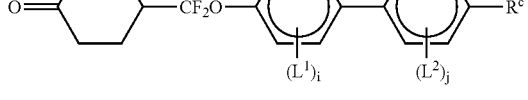

Vb

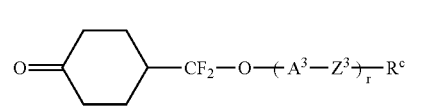

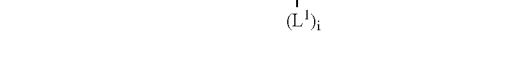

Vc1

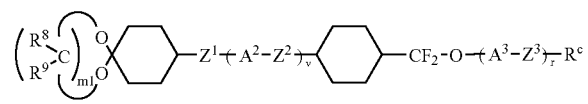

The corresponding compounds in which the carbonyl compound is protected as the ketal are likewise covered as preferred, but are not shown explicitly for reasons of clarity.

Furthermore, preferred compounds of the formulae Vc1 and Vc are the following carbonyl compounds, where the corresponding compounds containing a carbonyl function protected as the ketal are likewise preferred:

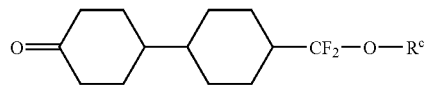 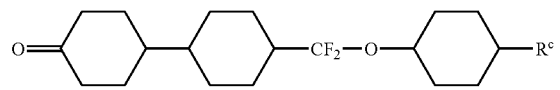
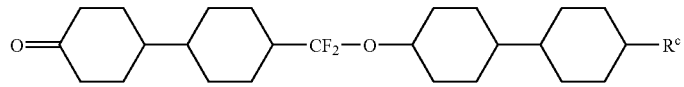
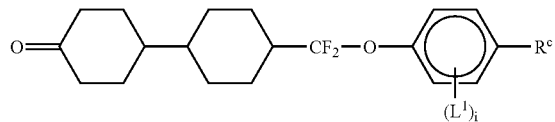
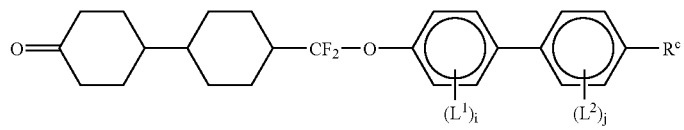
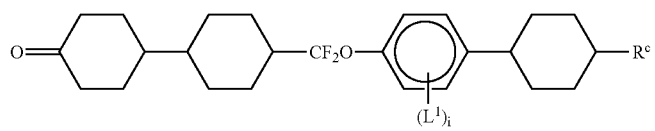
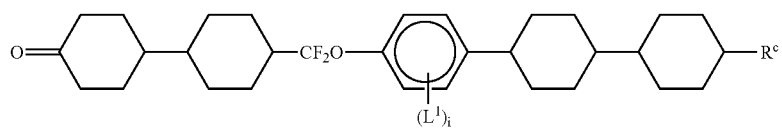
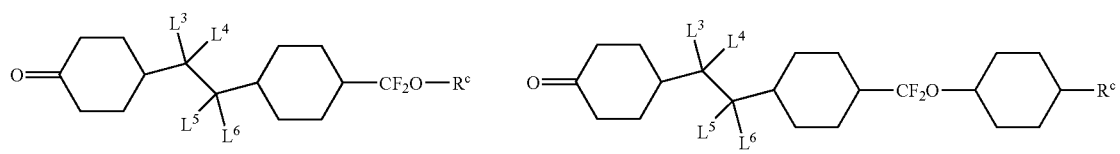
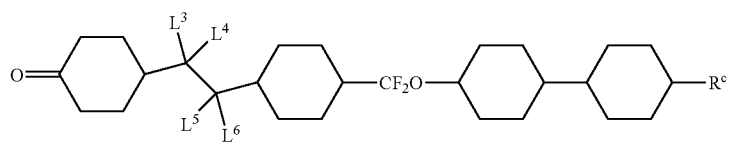
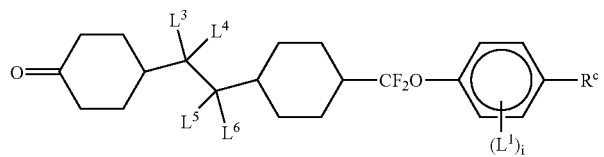

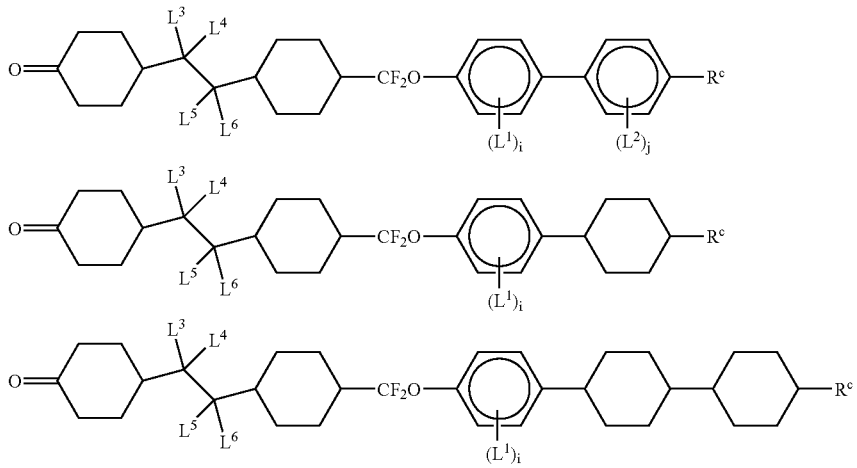

In the above formulae, $L^3$, $L^4$, $L^5$ and $L^6$, independently of one another, are as defined above for $L^1$ and $L^2$, preferably H or F. Particularly preferred meanings of the group

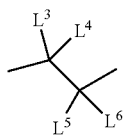

are —CH$_2$—CH$_2$—, —CF$_2$—CH$_2$—, —CH$_2$—CF$_2$— or —CF$_2$—CF$_2$—.

Likewise novel is the diketone of the formula Ic.1

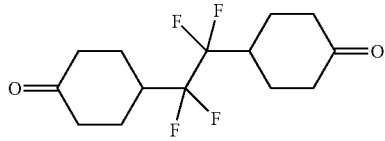

and the corresponding ketals of the formula Ic1.1

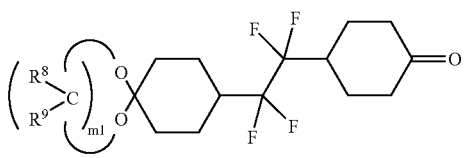

in which $R^8$, $R^9$ and m1 are as defined above, as starting compounds for the synthesis according to the invention, in particular of the compounds mentioned above containing a 1,2-biscyclohexyltrifluoroethylene group.

Particularly preferred compounds of the formula Ic1.1 are those of the formulae Ic1.1a to Ic1.1c

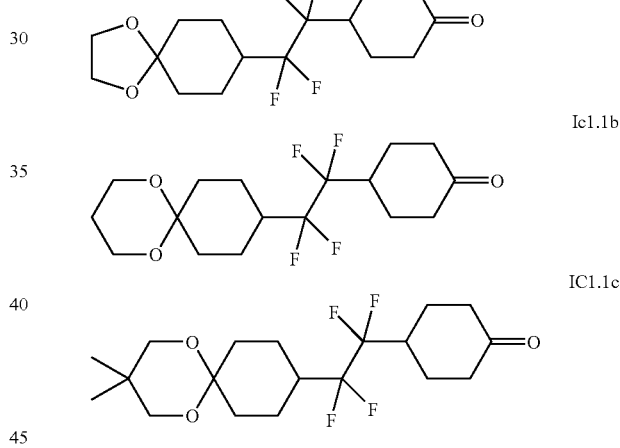

The following working examples are intended to illustrate the invention without representing a limitation. Above and below, percentages are per cent by weight. All temperatures are indicated in degrees Celsius. C=crystalline state, N=nematic phase and I=isotropic phase. The data between these symbols represent the transition temperatures. Δε denotes dielectric anisotropy (1 kHz, 20° C.) and Δn denotes optical anisotropy (589 nm, 20° C.).

"Conventional work-up" means that water is added if necessary, the pH is adjusted, if necessary, to between 1 and 11, depending on the constitution of the end product, the mixture is extracted with a suitable solvent, for example dichloromethane, diethyl ether, methyl tert-butyl ether or toluene, the phases are separated, the organic phase is dried and evaporated, and the product is purified by distillation under reduced pressure or crystallisation and/or chromatography.

The abbreviations THF for tetrahydrofuran, MTB for methyl tert-butyl ether and DBH for 1,3-dibromo-5,5-dimethylhydantoin are used.

WORKING EXAMPLES

1. Synthesis of the Liquid-Crystalline Compound of the Formula V.1

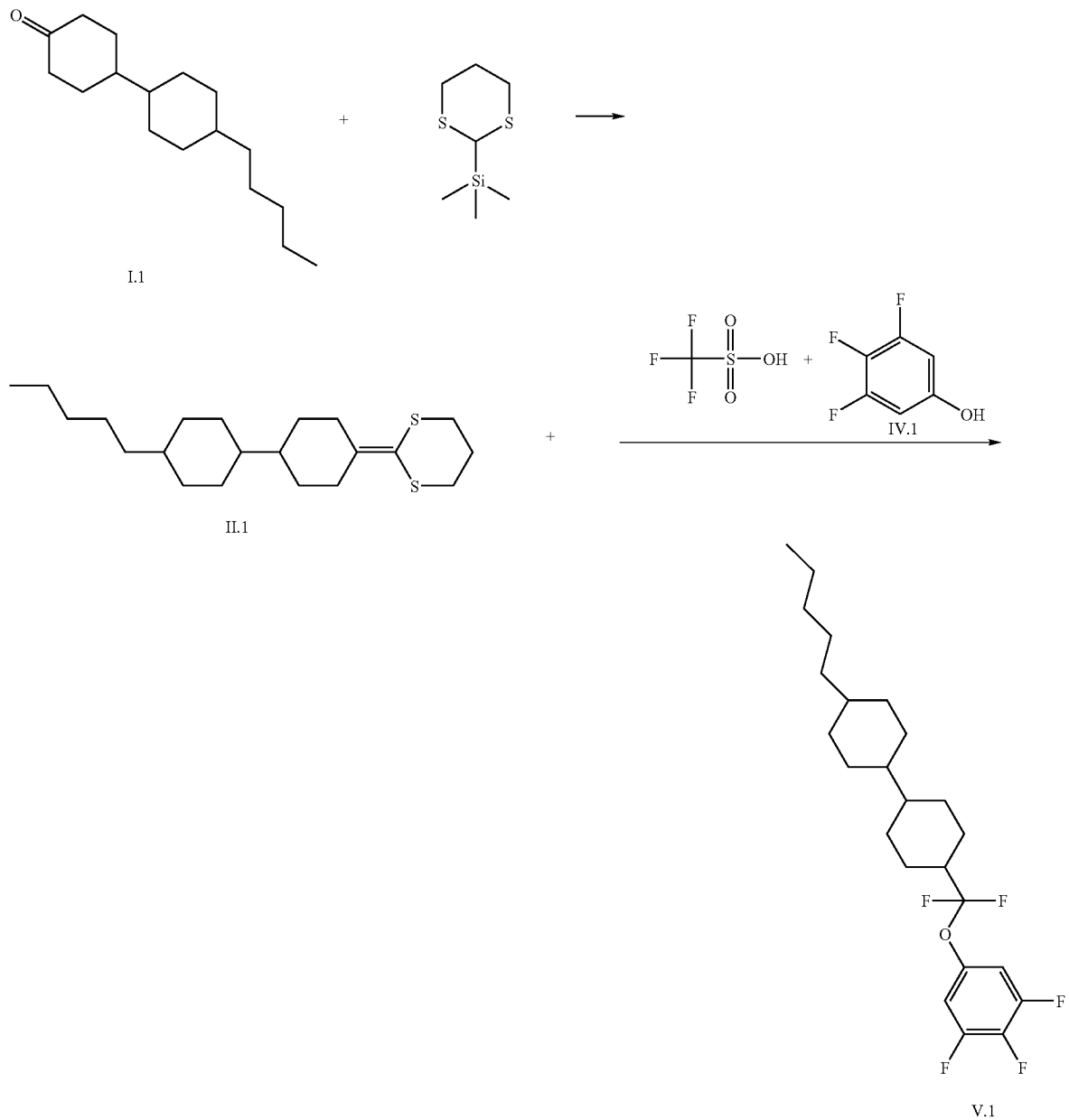

1.1 Preparation of the Compound II.1

0.075 mol of 2-trimethylsilyl-1,3-dithiane were dissolved in 150 ml of THF, and butyllithium (0.078 mol as a 15% solution in n-hexane) was added dropwise at −70° C. The mixture was allowed to warm gradually to 0° C. over the course of 4 hours and was re-cooled to −70° C., and the ketone was added dropwise to 50 ml of THF. A further 100 ml of THF were added. When the addition was complete, the cooling was removed, and the mixture was stirred overnight. The mixture was subsequently hydrolysed using 50 ml of saturated sodium hydrogen carbonate solution, 500 ml of petroleum ether were added, and the mixture was washed three times with 100 ml of water in each case and dried over sodium sulfate. The solvent was removed under reduced pressure, and the slightly yellow crude product was recrystallised from n-hexane, giving colourless needles.

1.2 Preparation of the Compound V.1

The ketene dithioketal II.1 (2.84 mmol) was dissolved in 15 ml of dichloromethane, and 2.84 mmol of trifluoromethanesulfonic acid were added with ice-cooling. After 15 minutes, the cooling was removed, and the mixture was stirred at room temperature for 30 minutes. The mixture was subsequently cooled to −70° C., a mixture of triethylamine (5.10 mmol) and trifluorophenol (4.25 mmol as a 90% solution in toluene) in 3 ml of dichloromethane was added, and the mixture was stirred at −70° C. for 1 hour. Triethylamine trishydrofluoride (14.18 mmol) was then added, and, after 5 minutes, DBH (14.18 mmol), suspended in 15 ml of dichloromethane, was added in portions over the course of about 30 minutes. The batch was stirred for a further 60 minutes and allowed to warm to −20° C., and the orange solution was added with stirring to 50 ml of ice-cold 1 molar sodium hydroxide solution. The organic phase was separated off, and the aqueous phase was extracted three times with dichloromethane. The combined organic phases were filtered, washed twice with saturated sodium chloride solution and dried over sodium sulfate. The solvent was removed under reduced pressure, and the residue was filtered through silica gel with n-hexane, giving a colourless oil, which slowly crystallised.

2. Preparation of the Compound V.2

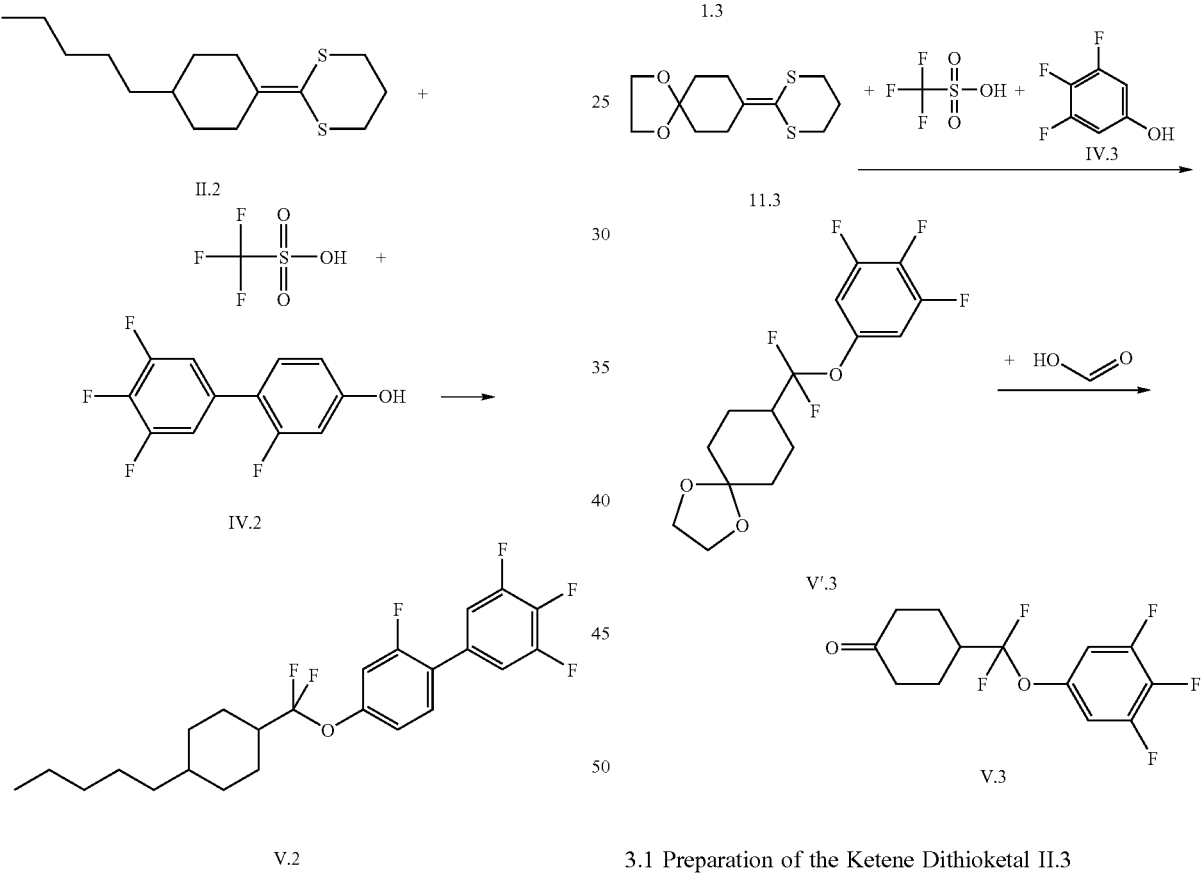

5.00 mmol of the ketene dithioketal II.2 were dissolved in 50 ml of dichloromethane, and 5.00 mmol of trifluoromethanesulfonic acid were added dropwise with ice cooling. After 15 minutes, the cooling was removed, and the mixture was stirred at room temperature for 30 minutes. The mixture was subsequently cooled to −70° C., a mixture of triethylamine (9.00 mmol) and 7.50 mmol of the phenol compound IV.6 in 10 ml of dichloromethane was added, and the mixture was stirred at −70° C. for 1 hour. Triethylamine trishydrofluoride (25.00 mmol) was then added, and, after 5 minutes, DBH (25.00 mmol), suspended in 15 ml of dichloromethane, was added in portions over the course of about 20 minutes. The batch was stirred for a further 60 minutes and allowed to warm to −20° C., and the orange solution was added with stirring to 100 ml of ice-cold 1 molar sodium hydroxide solution. The organic phase was separated off, and the aqueous phase was extracted three times with dichloromethane. The combined organic phases were filtered, washed twice with saturated sodium chloride solution and dried over sodium sulfate. The solvent was removed under reduced pressure. The residue was recrystallised from heptane at −60° C.

3. Preparation of the Compound V.3

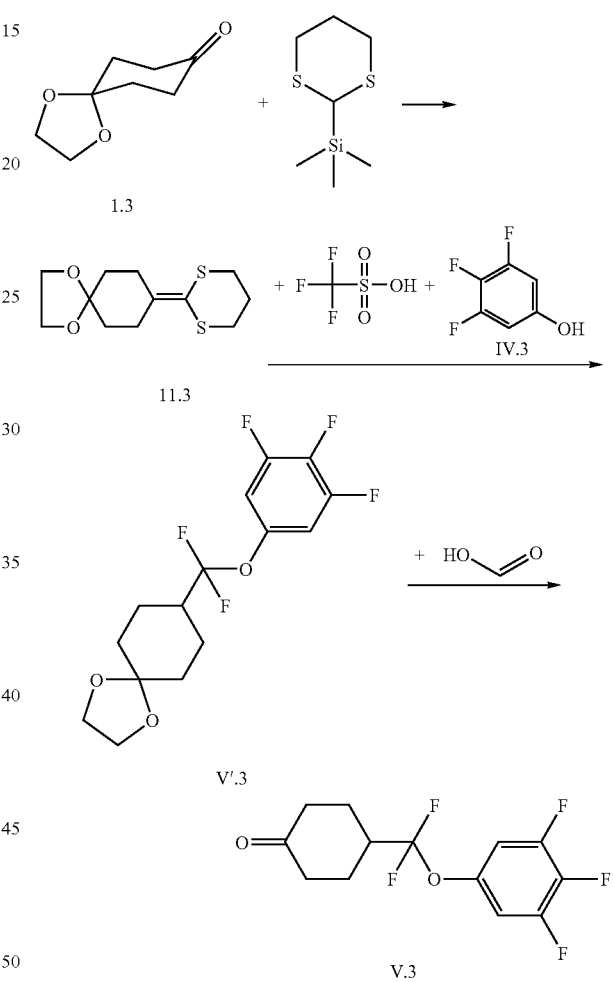

3.1 Preparation of the Ketene Dithioketal II.3

0.130 mol of 2-trimethylsilyl-1,3-dithiane were introduced into 400 ml of THF, and 0.130 mol of butyllithium (15% solution in n-hexane) was added dropwise at −70° C. The mixture was stirred at −70° C. for 1 hour, and allowed to rise slowly to −15° C. 0.130 mol of the cyclohexanedione I.3, whose first carbonyl function was protected as the ketal with 1,2-ethanediol, dissolved in 100 ml of THF was added dropwise, again at −70° C. The cooling bath was removed, and the mixture was stirred overnight at about 20° C.

The batch was hydrolysed using 200 ml of NaHCO$_3$ solution. 700 ml of MTB ether were then added, and the mixture was washed twice with 200 ml of water in each case. The aqueous phases were then extracted twice with ether.

The combined organic phases were dried using sodium sulfate, filtered and evaporated.

$^1$H-NMR (CDCl$_3$, 250 MHz, 20° C.): δ=3.95 (s, 4H), 2.87 (mc, 4H), 2.61 (mc, 4H), 2.17–2.08 (m, 2H), 1.68 (t, J=6.6 Hz, 4H).

3.2 Preparation of the ether V'.3

0.093 mol of the ketene dithioketal II.3 were dissolved in 300 ml of dichloromethane, and 0.093 mol of trifluoromethanesulfonic acid were added with stirring at +5° C.

The temperature was allowed to rise to about 20° C., and stirring was continued for one hour. After the mixture had cooled to –70° C., a mixture of trifluorophenol IV.3 (0.140 mol) and 0.167 mol of triethylamine in 30 ml of dichloromethane was added dropwise, and the mixture was stirred at –70° C. for a further hour. 0.465 mol of triethylamine trishydrofluoride was subsequently added dropwise. After about 10 minutes, 0.465 mol of DBH, suspended in 170 ml of dichloromethane, was added distributed over one hour, and the mixture was stirred at –70° C. for one hour.

The reaction mixture at a temperature of –20° C. was added with stirring to 300 ml of 1 molar NaOH solution. The aqueous phase was separated off and extracted once with dichloromethane. The combined organic phases were washed with water and dried using sodium sulfate, filtered twice and evaporated. The product was recrystallised from heptane. Melting point: 67° C.

$^{19}$F-NMR (CDCl$_3$, 235 MHz, 20° C.): δ=–78.4 (d, J=8.3 Hz, 2F), –133.5 (mc, 2F), –164.9 (mc, 1F).

3.3 Preparation of the Ether V.3

0.017 mol of the ether V'.3, 100 ml of toluene and 1.1 mol of 98–100% formic acid were stirred together overnight. The formic acid was separated off, and the mixture was extracted twice with toluene.

The combined organic phases were washed twice with water, dried using sodium sulfate, filtered and evaporated.

$^{19}$F-NMR (CDCl$_3$, 235 MHz, 20° C.): δ=76.1 (d, J=8.4 Hz, 2F), –131.2 (mc, 2F), –162.4 (mc, 1F).

4. Preparation of the Compound V.4

4.1 Preparation of the Ketene Dithioketal II II.4

130 mmol of 2-trimethylsilyl-1,3-dithiane were dissolved in 500 ml of THF, and 130 mmol of butyllithium as a 15% solution in n-hexane were added dropwise at –70° C. The mixture was allowed to warm gradually to 0° C. over the course of 4 hours and re-cooled to –70° C., and the ketone I.4 (60 mmol) in 100 ml of THF was added dropwise, during which a colourless precipitate deposited. When the addition was complete, the cooling was removed, and the mixture was stirred overnight. 500 ml of ice-water were subsequently added to the batch, which was extracted with dichloromethane until all the precipitate had dissolved. The combined organic phases were washed twice with saturated sodium chloride solution and dried over sodium sulfate. The solvent was removed under reduced pressure, and the slightly yellow crude product was purified by recrystallisation from dichloromethane, giving colourless flakes.

4.2 Preparation of the Compound V.4

17.4 mmol of the ketene dithioketal II.4 were suspended in 100 ml of dichloromethane, and 34.8 mmol of trifluoromethanesulfonic acid were added dropwise with ice cooling. The clear yellow solution was subsequently stirred at room temperature for 1 hour. The batch was then cooled to –70° C., and a solution of 4-nitrophenol IV.4 (52.2 mmol) and triethylamine (62.6 mmol) in 20 ml of dichloromethane was added dropwise. After 1 hour, triethylamine trishydrofluoride (152.0 mmol) was slowly added, and a suspension of DBH (173.8 mmol) in 70 ml of dichloromethane was subsequently added in portions over the course of 30 minutes. After the batch had been stirred for 60 minutes, it was allowed to warm to –20° C., and the orange suspension was carefully added to an ice-cold mixture of 500 ml of approximately 1 molar sodium hydroxide solution and 50 ml of sodium hydrogensulfite solution. The pH was adjusted to 7 using 32% sodium hydroxide solution, the aqueous phase was separated of and extracted three times with pentane, and the combined organic phases were dried over sodium sulfate. The solvent was removed under reduced pressure, and the residue was filtered through silica gel with dichloromethane/n-heptane (1:1). The crude product was recrystallised from dichloromethane/n-hexane, giving pale yellow crystals (melting point: 164° C.). 5. Preparation of the compound V.5

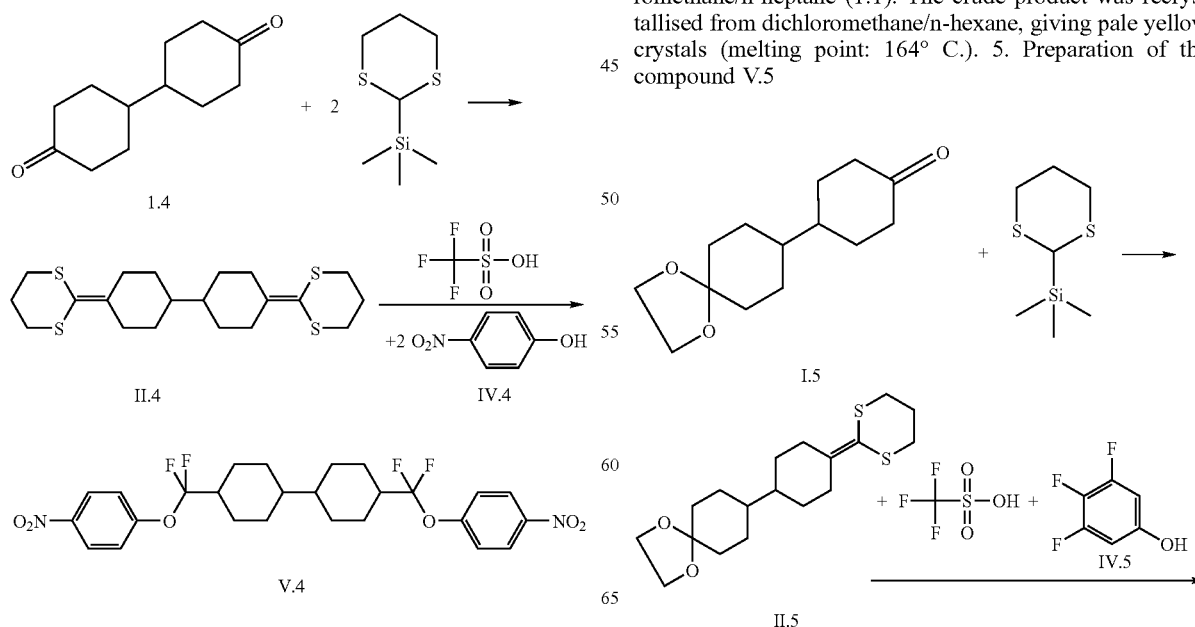

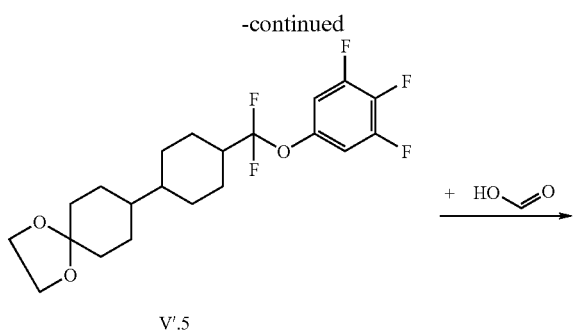

$^{19}$F-NMR (CDCl$_3$, 235 MHz, 20° C.): δ=−79.4 (d, J=8.4 Hz, 2F), −133.8 (mc, 2F), −165.2 (mc, 1F).

6. Synthesis of the Ether V.6

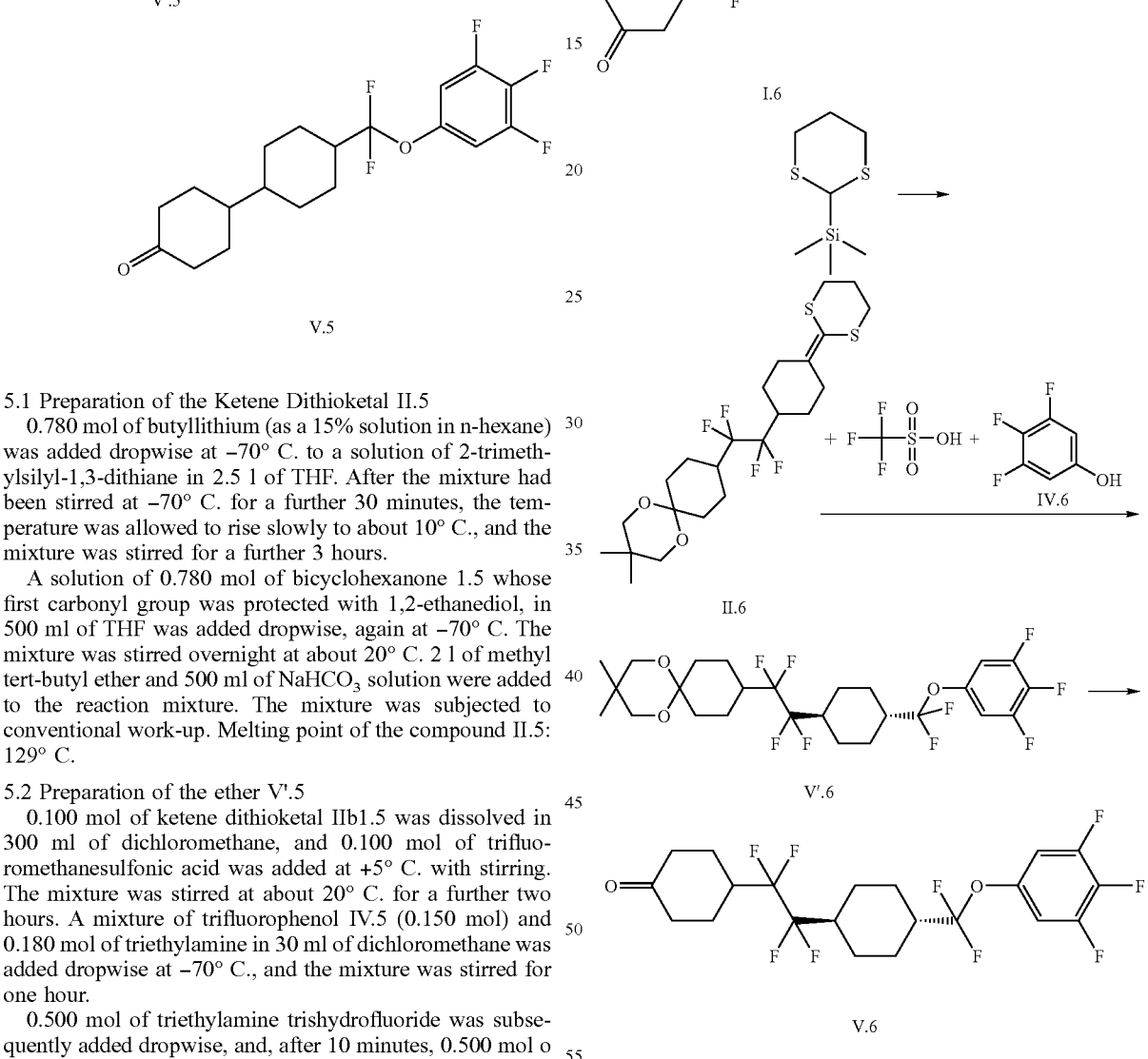

5.1 Preparation of the Ketene Dithioketal II.5

0.780 mol of butyllithium (as a 15% solution in n-hexane) was added dropwise at −70° C. to a solution of 2-trimethylsilyl-1,3-dithiane in 2.5 l of THF. After the mixture had been stirred at −70° C. for a further 30 minutes, the temperature was allowed to rise slowly to about 10° C., and the mixture was stirred for a further 3 hours.

A solution of 0.780 mol of bicyclohexanone I.5 whose first carbonyl group was protected with 1,2-ethanediol, in 500 ml of THF was added dropwise, again at −70° C. The mixture was stirred overnight at about 20° C. 2 l of methyl tert-butyl ether and 500 ml of NaHCO$_3$ solution were added to the reaction mixture. The mixture was subjected to conventional work-up. Melting point of the compound II.5: 129° C.

5.2 Preparation of the ether V'.5

0.100 mol of ketene dithioketal IIb1.5 was dissolved in 300 ml of dichloromethane, and 0.100 mol of trifluoromethanesulfonic acid was added at +5° C. with stirring. The mixture was stirred at about 20° C. for a further two hours. A mixture of trifluorophenol IV.5 (0.150 mol) and 0.180 mol of triethylamine in 30 ml of dichloromethane was added dropwise at −70° C., and the mixture was stirred for one hour.

0.500 mol of triethylamine trishydrofluoride was subsequently added dropwise, and, after 10 minutes, 0.500 mol o DBH, suspended in 170 ml of dichloromethane, was added distributed over 1 hour, and the reaction mixture was stirred at −70° C. for a further hour and introduced at a temperature of about −20° C. into 300 ml of 1 molar NaOH with stirring. The mixture was subjected to conventional work-up.

5.3 Cleavage of the Ketal to Give the Ether V.5

200 ml of pure formic acid were added to 0.083 mol of the ketal V'.5, dissolved in 250 ml of toluene. The reaction mixture was stirred overnight at about 20° C. The formic acid was subsequently separated off and extracted twice with toluene. The combined organic phases were subjected to conventional work-up.

6.1 Preparation of the Ketene Dithioketal II.6

0.131 mol of n-butyllithium as a 15% solution in n-hexane was added dropwise at −70° C. to 0.129 mol of 2-trimethylsilyl-1,3-dithiane in 400 ml of THF, and the mixture was subsequently stirred at −70° C. for 30 minutes. The temperature of the reaction mixture was increased slowly to from −15 to −5° C., and the mixture was stirred at this temperature for 3 hours. 0.128 mol of the dicarbonyl compound I.6, mono-protected as the ketal and dissolved in 100 ml of THF, was added dropwise, again at −70° C. The temperature was subsequently increased slowly to about 20°

C., and the mixture was stirred overnight. 500 ml of methyl tert-butyl ether and 250 ml of aqueous $NaHCO_3$ solution were added to the reaction mixture, which was subsequently subjected to conventional work-up.

$^{19}$F-NMR ($CDCl_3$, 235 MHz, 20° C.): δ=–115.9 (mc, 2F), –116.3 (mc, 2F).

6.2 Preparation of the Ether V'.6

13.1 mmol of trifluoromethanesulfonic acid were added dropwise at about 0° C. to 13.1 mmol of ketene dithioketal II.6, dissolved in 60 ml of dichloromethane. After the mixture had been stirred for 15 minutes, it was warmed slowly to 20° C. and stirred for a further 60 minutes. A mixture of 22.6 mmol of triethylamine, 19.7 mmol of trifluorophenol IV.6 and 60 ml of dichloromethane was added at –70° C., and the mixture is stirred for one hour. 65.5 mmol of triethylamine trishydrofluoride were subsequently added, and, after 5 minutes, 3.4 ml of bromine, dissolved in 30 ml of dichloromethane, were added over the course of 10 minutes. After the reaction mixture had been stirred for a further 16 minutes, it was slowly warmed to –20° C. and added with stirring to a mixture of 20 ml of saturated sodium hydrogensulfite solution and 150 ml of 2 molar sodium hydroxide solution. The work-up was carried out in the conventional way.

$^{19}$F-NMR ($CDCl_3$, 235 MHz, 20° C.): δ=–78.4 (d, J=8.2 Hz, 2F), –115.0 (mc, 2F), –115.8 (mc, 2F), –132.5 (mc, 2F), –163.9 (mc, 1F).

6.3 Cleavage of the Ketal to Give the Product V.6

8.90 mmol of the ketal V'.6 in 30 ml of toluene were stirred for about 48 hours together with 3.8 ml of pure formic acid. The formic phase was subsequently separated off, dilute with 100 ml of water and extracted three times with toluene. The product was obtained in the usual way from the combined toluene phases.

$^{19}$F-NMR ($CDCl_3$, 235 MHz, 20° C.): δ=–81.1 (d, J=8.2 Hz, 2F), –117.2 (mc, 2F), –118.1 (mc, 2F), –135.2 (mc, 2F), –166.5 (mc, 1F).

7. Synthesis of th compound V.7

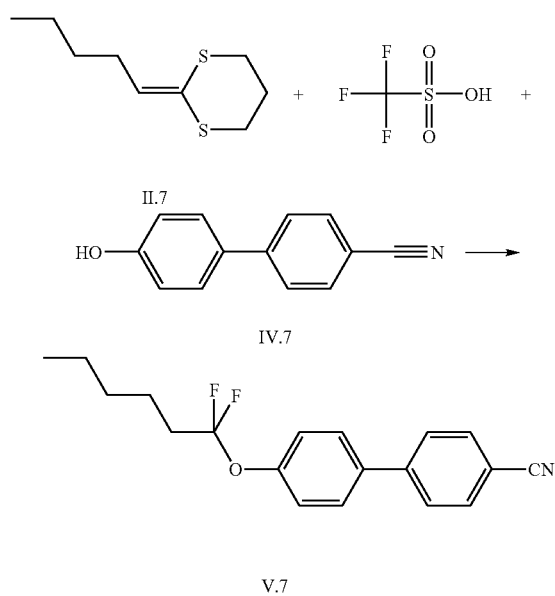

20 mmol of trifluoromethanesulfonic acid were slowly added with ice-cooling to a solution of 19 mmol of 2-pentylidene-1,3-dithiane II.7 in 35 ml of dichloromethane, and the mixture was stirred for 20 minutes. The batch was subsequently cooled to –70° C. and added dropwise over the course of 15 minutes to a solution of 30 mmol of triethylamine and 4'-hydroxybiphenyl-4-carbonitrile (25 mmol) in 50 ml of dichloromethane. After a further 45 minutes, 96 mmol of triethylamine trishydrofluoride were added slowly, and a suspension of 96 mmol of DBH in 60 ml of dichloromethane was then added in portions over the course of 60 minutes. After the batch had been stirred for 60 minutes, it was warmed to –20° C., and the orange suspension was added carefully to an ice-cold mixture of 500 ml of approximately 1M sodium hydroxide solution and 50 ml of sodium hydrogensulfite solution. The aqueous phase was separated off and extracted three times with dichloromethane, and the combined organic phases were subjected to conventional work-up (C 47 N 63 I, Δε=17.7, Δn=0.1844)

$^{19}$F-NMR ($CDCl_3$, 235 MHz, 20° C.): δ=–71.0 ppm (t, J=11.3 Hz, 2F, —$CF_2O$—).

MS (EI): m/e (%)=315 [M$^+$] (33), 195 [M$^+$+H —$C_5H_{11}CF_2$] (100).

What is claimed is:

1. A process for preparing a compound containing at least one —$CF_2$—O— bridge-comprising
   a) adding an acid onto at least one ketene dithioketal to form a bis(alkylthio)carbenium salt,
   b) reacting the resultant bis(alkylthio)carbenium salt with at least one compound having at least one hydroxyl group in the presence of a base to form a dithioorthoester,
   c) and subsequently subjecting the resultant dithioorthoester to oxidative fluorodesulfurization using a fluorinating agent and an oxidant to give the corresponding compound containing at least one —$CF_2$—O— bridge.

2. A process according to claim 1, wherein the ketene dithioketal is of formula II

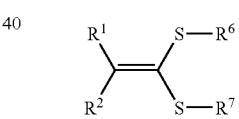

II in which
R$^1$ and
R$^2$, independently of one another, are straight-chain, branched or cyclic alkyl having from 1 to 25 carbon atoms, where R$^1$ and R$^2$ may be bridged to one another in such a way that the

group is a cyclic alkyl having 4 to 8 carbon atoms in the ring, and/or in which one or more H atoms may be replaced by halogen, —CN, further substituted or unsubstituted alkyl and/or aryl radicals, and/or in which one or more non-adjacent —$CH_2$— groups may be replaced, independently of one another, by —CO—, —O—CO—, —CO—O—, —O—, —S—, —CH=CH—, —C≡C—, —NH— or —N($CH_3$)—, and/or aryl, which may be monosubstituted or polysubstituted by halogen, straight-chain, branched and/or cyclic alkyl and/or aryl, which may be substituted, and in which one or more CH groups may be replaced by N, where one of the radicals $R^1$ and $R^2$ may alternatively be H, $R^6$ and $R^7$, independently of one another, are straight-chain, branched or cyclic alkyl having 1 to 12 carbon atoms, where $R^6$ and $R^7$ may be bridged to one another in such a way that the

group is a 4- to 8-membered ring, and/or in which one or more H atoms may be replaced by halogen or further substituted or unsubstituted alkyl and/or aryl radicals, and/or in which one or more non-adjacent —$CH_2$— groups may be replaced, independently of one another, by —CO—, —O—, —S—, —CH=CH—, —C≡C—, —NH— or —N($CH_3$)—, and/or aryl, which may be monosubstituted or polysubstituted by halogen or straight-chain, branched and/or cyclic alkyl and/or aryl.

3. A process according to claim 1, wherein the acid added onto the ketene dithioketal is HY, in which $Y^-$ is a non-coordinating or weakly coordinating anion.

4. A process according to claim 3, wherein $Y^-$ is a halide, tetrafluoroborate, hexafluorophosphate, perchlorate or alkyl- or arylcarboxylate or alkyl- or arylsulfonate anion, where one or more or all of the H atoms in the alkyl or aryl groups may be substituted by fluorine or chlorine.

5. A process according to claim 1, wherein the bis(alkylthio)carbenium salt is of formula III

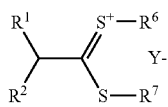

III $R^1$ and $R^2$, independently of one another, are straight-chain, branched or cyclic alkyl having from 1 to 25 carbon atoms, where $R^1$ and $R^2$ may be bridged to one another in such a way that the

group is a cyclic alkyl having 4 to 8 carbon atoms in the ring, and/or in which one or more H atoms may be replaced by halogen, —CN, further substituted or unsubstituted alkyl and/or aryl radicals, and/or in which one or more non-adjacent —$CH_2$— groups may be replaced, independently of one another, by —CO—, —O—CO—, —CO—O—, —O—, —S—, —CH=CH—, —C≡C—, —NH— or —N($CH_3$)—, and/or aryl, which may be monosubstituted or polysubstituted by halogen, straight-chain, branched and/or cyclic alkyl and/or aiyl, which may be substituted, and in which one or more CH groups may be replaced by N, where one of the radicals $R^1$ and $R^2$ may alternatively be H, $R^6$ and $R^7$, independently of one another, are straight-chain, branched or cyclic alkyl having ito 12 carbon atoms, where $R^6$ and $R^7$ may be bridged to one another in such a way that the

group is a 4- to 8-membered ring, and/or in which one or more H atoms may be replaced by halogen or further substituted or unsubstituted alkyl and/or aryl radicals, and/or in which one or more non-adjacent —$CH_2$— groups may be replaced, independently of one another, by —CO—, —O—, —S—, —CH=CH—, —C≡C—, —NH— or —N($CH_3$)—, and/or aryl, which may be monosubstituted or polysubstituted by halogen or straight-chain, branched and/or cyclic alkyl and/or aryl, and $Y^-$ is a non-coordinating or weakly coordinating anion.

6. A process according to claim 1, wherein the compound containing at least one hydroxyl group is an alkyl or aryl alcohol of formula IV $$R^3\text{—OH} \qquad (IV),$$

wherein $R^3$ is an alkyl or aryl radical that may be substituted.

7. A process according to claim 1, wherein the dithioorthoester is of formula VI

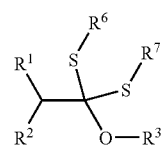

VI in which $R^1$ and $R^2$, independently of one another, are straight-chain, branched or cyclic alkyl having from 1 to 25 carbon atoms, where $R^1$ and $R^2$ may be bridged to one another in such a way that the

group is a cyclic alkyl having 4 to 8 carbon atoms in the ring, and/or in which one or more H atoms may be replaced by halogen, —CN, further substituted or unsubstituted alkyl and/or aryl radicals, and/or in which one or more non-adjacent —$CH_2$— groups may be replaced, independently of one another, by —CO—, —O—CO—, —CO—O—, —O—, —S—, —CH=CH—, —C≡C—, —NH— or —N(CH$_3$)—, and/or aryl, which may be monosubstituted or polysubstituted by halogen, straight-chain, branched and/or cyclic alkyl and/or aryl, which may be substituted, and in which one or more CH groups may be replaced by N, where one of the radicals R$^1$ and R$^2$ may alternatively be H, R$^6$ and R$^7$, independently of one another, are straight-chain, branched or cyclic alkyl having 1 to 12 carbon atoms, where R$^6$ and R$^7$ may be bridged to one another in such a way that the

group is a 4- to 8-membered ring, and/or in which one or more H atoms may be replaced by halogen or further substituted or unsubstituted alkyl and/or aryl radicals, and/or in which one or more non-adjacent —CH$_2$— groups may be replaced, independently of one another, by —CO—, —O—, —S—, —CH=CH—, —C≡C—, —NH— or —N(CH$_3$)—, and/or aryl, which may be monosubstituted or polysubstituted by halogen or straight-chain, branched and/or cyclic alkyl and/or aryl, and R$^3$ is an alkyl or aryl radical that may be substituted.

8. A process according to claim 1, wherein the oxidant is a compound which liberates a halonium equivalent.

9. A process according to claim 1, wherein the fluorinating agent is selected from hydrogen fluoride, aliphatic and aromatic amine/hydrogen fluoride complexes, pyridine/, triethylamine/, melamine/ and polyvinylpyridine/hydrogen fluoride complexes.

10. A process according to claim 1, wherein compound containing at least one hydroxyl group is of the formula IVa

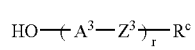

IVa in which

R$^c$ is H, halogen, —CN, —NCS, —SF$_5$ or alkyl having from 1 to 18 carbon atoms, in which one or two non-adjacent —CH$_2$— groups may be replaced by —O—, —S—, —CO—, —O—CO—, —CO—O—, -E- and/or —C≡C— and/or in which one or more H atoms may be replaced by halogen and/or —CN, E is CR$^4$=CR$^5$ or CHR$^4$—CHR$^5$, R$^4$ and R$^5$ are each, independently of one another, H, alkyl having 1–6 carbon atoms, F, Cl, Br, CF$_3$ or CN, Z$^3$ is —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, A$^3$ is 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where one or more H atoms in these groups may be substituted by halogen, —CN and/or alkyl having 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and r is 0, 1 or 2, with the proviso that, in the case where r=0, R$^c$ has the indicated meaning of alkyl, but in which the carbon atom in the 1-position is not replaced by a heteroatom.

11. A process according to claim 1, wherein the compound containing at least one hydroxyl group has two hydroxyl groups.

12. A process according to claim 11, wherein the compound containing two hydroxyl groups is of the formula IVd

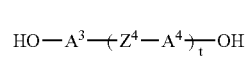

IVd in which

A$^3$ is 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where one or more H atoms in these groups may be substituted by halogen, —CN and/or alkyl having 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and A$^4$ has one of the meanings indicated for A$^3$, and Z$^4$ is —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, and t is 0, 1 or 2.

13. A process according to claim 1, wherein the ketene dithioketal is obtained from a carbonyl compound.

14. A process according to claim 13, wherein the ketene dithioketal is obtained from a carbonyl compound of formula I

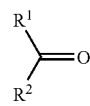

I in which

R[1] and

R[2], independently of one another, are straight-chain, branched or cyclic alkyl having from 1 to 25 carbon atoms, where R[1] and R[2] may be bridged to one another in such a way that the

group is a cyclic alkyl having 4 to 8 carbon atoms in the ring, and/or in which one or more H atoms may be replaced by halogen, —CN, further substituted or unsubstituted alkyl and/or aryl radicals, and/or in which one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and/or aryl, which may be monosubstituted or polysubstituted by halogen, straight-chain, branched and/or cyclic alkyl and/or aryl, which may be substituted, and in which one or more CH groups may be replaced by N, where one of the radicals R[1] and R[2] may alternatively be H.

15. A process according to claim 13, wherein the carbonyl compound is of formula Ia

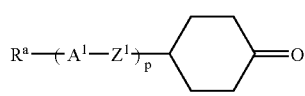

in which

R$^a$ is H, halogen, —CN or alkyl having 1 to 18 carbon atoms, in which one or two non-adjacent —CH$_2$— groups may be replaced by —O—, —S—, —CO—, —O—CO—, —CO—O—, -E- and/or —C≡C— and/or in which one or more H atoms may be replaced by halogen and/or CN, E is CR[4]=CR[5] or CHR[4]—CHR[5], R[4] and R[5] are each, independently of one another, H, alkyl having 1–6 carbon atoms, F, Cl, Br, CF$_3$ or CN, Z[1] is —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, A[1] is 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where one or more H atoms in these groups may be substituted by halogen, —CN and/or alkyl having from 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and p is 0, 1 or 2.

16. A process according to claim 13, wherein the carbonyl compound has two or more carbonyl groups.

17. A process according to claim 13, wherein the carbonyl compound has two or more carbonyl groups, which is a cyclohexanedione of formula Ib

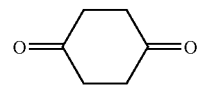

or a compound of formula Ic

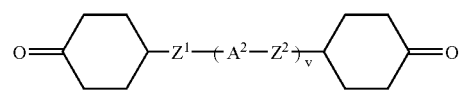

in which

Z[1] and

Z[2] each, independently of one another is —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, A[2] is 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where one or more H atoms in these groups may be substituted by halogen, —CN and/or alkyl having from 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH—, —C≡C—, —NH— or —N(CH$_3$)—, and v is 0, 1 or 2.

18. A process according to claim 16, wherein one or more carbonyl groups of the carbonyl compound are protected as a ketal before the conversion into the corresponding ketene dithioketal, with at least one carbonyl group remaining unprotected for conversion into the ketene dithioketal.

19. A process according to claim 13, wherein the ketene dithioketal is obtained from the carbonyl compound by reaction with substituted or unsubstituted 2-silyl-1,3-dithiane.

20. A ketene dithioketal of formula IIa

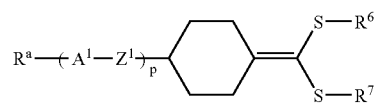

and/or a corresponding bis(alkylthio)carbenium salt of formula IIIa

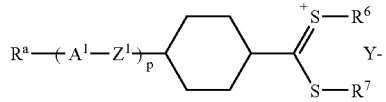 IIIa in which

R$^a$ is halogen, —CN or alkyl having 1 to 18 carbon atoms, in which one or two non-adjacent —CH$_2$— groups may be replaced by —O—, —S—, —CO—, —O—CO—, —CO—O—, -E- and/or —C≡C—, and/or in which one or more H atoms may be replaced by halogen and/or CN, E is CR$^4$=CR$^5$ or CHR$^4$—CHR$^5$, R$^4$ and R$^5$ are each, independently of one another, H, alkyl having 1–6 carbon atoms, F, Cl, Br, CF$_3$ or CN, and Z$^1$ is —O—CO—, —CO—O—, —C$_2$H$_4$—, —CH$_2$—CF$_2$—, —CF$_2$—CH$_2$—, —CF$_2$—CF$_2$—, —CH$_2$—O—, —CF$_2$—O—, —O—CH$_2$—, —O—CF$_2$—, —CH=CH—, —CF=CH—, —CH=CF—, —CF=CF—, —C≡C— or a single bond, A$^1$ is 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where one or more H atoms in these groups may be substituted by halogen, —CN and/or alkyl having 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH—, —C≡C—, —NH— or p is 0, 1 or 2, and R$^6$ and R$^7$, independently of one another, are straight-chain, branched or cyclic alkyl having 1 to 12 carbon atoms, where R$^6$ and R$^7$ may be bridged to one another in such a way that the

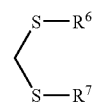

group is a 4- to 8-membered ring, and/or in which one or more H atoms may be replaced by halogen or further substituted or unsubstituted alkyl and/or aryl radicals, and/or in which one or more non-adjacent —CH$_2$— groups may be replaced, independently of one another, by —CO—, —O—, —S—, —CH=CH—, —C≡C—, —NH— or —N(CH$_3$)—, and/or aryl, which may be monosubstituted or polysubstituted by halogen or straight-chain, branched and/or cyclic alkyl and/or aryl, and Y$^-$ is a non-coordinating or weakly coordinating anion.

21. A process according to claim 1, wherein subjecting the resultant dithioorthoester to oxidative fluorodesulfurisation using a fluorinating agent and an oxidant is performed in situ.

22. A process according to claim 8, wherein the oxidant is selected from dimethyldibromohydantoin, N-chlorosuccinimide, N-bromosuccinimide, N-iodosuccinimide, dibromoisocyanuric acid, chlorine, bromine, SO$_2$Cl$_2$, SO$_2$ClF, nitrosonium and nitronium salts, organic and inorganic nitrites and chloramine-T.

23. A ketene dithioketal according to claim 20, wherein R$^a$ is halogen, —CN or alkyl having 2 to 18 carbon atoms, in which one or two non-adjacent —CH$_2$— groups may be replaced by —O—, —S—, —CO—, —O—CO—, —CO—O—, -E- and/or —C≡C—, and/or in which one or more H atoms may be replaced by halogen and/or CN.

* * * * *

UNITED STATES PATENT AND TRADEMARK OFFICE
CERTIFICATE OF CORRECTION

PATENT NO. : 7,105,708 B2  
APPLICATION NO. : 10/450266  
DATED : September 12, 2006  
INVENTOR(S) : Peer Kirsch Page 1 of 1

It is certified that error appears in the above-identified patent and that said Letters Patent is hereby corrected as shown below:

Column 42, line 2, reads "and/or aiyl," should read -- and/or aryl, --  
Column 42, line 9, reads "having ito" should read -- having 1 to --  
Column 43, line 53, reads "-C≡C- and/or" should read -- -C≡C-, and/or --  
Column 43, line 63, reads "-C≡C-or" should read -- -C≡C- or --  
Column 45, line 43, reads "-C≡C- and/or" should read -- -C≡C-, and/or --  
Column 45, line 55, reads "-C=C-" should read -- -C≡C- --  
Column 47, line 2, reads "lila" should read -- IIIa --  
Column 47, line 43, reads "-NH- or" should read -- -NH- or –N(CH$_3$)-, --

Signed and Sealed this

Twelfth Day of June, 2007

JON W. DUDAS  
*Director of the United States Patent and Trademark Office*